(12) United States Patent
Nakamura et al.

(10) Patent No.: US 11,241,518 B2
(45) Date of Patent: Feb. 8, 2022

(54) CARTILAGE REGENERATIVE MATERIAL

(71) Applicants: FUJIFILM Corporation, Tokyo (JP); JAPAN TISSUE ENGINEERING CO., LTD., Gamagori (JP)

(72) Inventors: Kentaro Nakamura, Ashigarakami-gun (JP); Hayato Miyoshi, Ashigarakami-gun (JP); Satoko Hada, Gamagori (JP); Masatoki Watanabe, Gamagori (JP)

(73) Assignees: FUJIFILM Corporation, Tokyo (JP); JAPAN TISSUE ENGINEERING CO., LTD., Gamagori (JP)

( * ) Notice: Subject to any disclaimer, the term of this patent is extended or adjusted under 35 U.S.C. 154(b) by 0 days.

(21) Appl. No.: 16/660,003

(22) Filed: Oct. 22, 2019

(65) Prior Publication Data
US 2020/0069841 A1 Mar. 5, 2020

Related U.S. Application Data

(60) Division of application No. 15/705,826, filed on Sep. 15, 2017, now abandoned, which is a continuation of application No. PCT/JP2016/058540, filed on Mar. 17, 2016.

(30) Foreign Application Priority Data

Mar. 18, 2015 (JP) .............................. JP2015-054874

(51) Int. Cl.
| | |
|---|---|
| *A61L 27/36* | (2006.01) |
| *A61K 38/39* | (2006.01) |
| *A61K 35/28* | (2015.01) |
| *A61K 38/17* | (2006.01) |
| *A61L 27/22* | (2006.01) |
| *A61L 27/38* | (2006.01) |
| *A61K 35/32* | (2015.01) |
| *A61L 27/54* | (2006.01) |
| *A61L 27/56* | (2006.01) |
| *A61F 2/30* | (2006.01) |
| *A61L 27/58* | (2006.01) |

(52) U.S. Cl.
CPC .......... *A61L 27/3654* (2013.01); *A61K 35/28* (2013.01); *A61K 35/32* (2013.01); *A61K 38/17* (2013.01); *A61K 38/39* (2013.01); *A61L 27/222* (2013.01); *A61L 27/3834* (2013.01); *A61L 27/3852* (2013.01); *A61L 27/54* (2013.01); *A61L 27/56* (2013.01); *A61F 2002/30766* (2013.01); *A61L 27/58* (2013.01); *A61L 2430/06* (2013.01)

(58) Field of Classification Search
None
See application file for complete search history.

(56) References Cited

U.S. PATENT DOCUMENTS

| | | |
|---|---|---|
| 5,447,966 A | 9/1995 | Hermes et al. |
| 6,387,693 B2 | 5/2002 | Rieser et al. |
| 2002/0177903 A1 | 11/2002 | Geistlich et al. |
| 2003/0050709 A1 | 3/2003 | Noth et al. |
| 2004/0062809 A1 | 4/2004 | Honiger et al. |
| 2004/0234577 A1 | 11/2004 | Geistlich et al. |
| 2006/0212125 A1 | 9/2006 | Okihana |
| 2007/0160681 A1 | 7/2007 | Park et al. |
| 2009/0228105 A1 | 9/2009 | Son et al. |
| 2011/0184381 A1 | 7/2011 | Shintani |
| 2012/0148639 A1 | 6/2012 | Tamada et al. |
| 2012/0165263 A1 | 6/2012 | Hiratsuka et al. |
| 2012/0329157 A1 | 12/2012 | Nakamura |
| 2013/0004549 A1 | 1/2013 | Nakamura et al. |
| 2013/0071441 A1 | 3/2013 | Iwazawa et al. |
| 2014/0378662 A1 | 12/2014 | Oya et al. |
| 2015/0352252 A1 | 12/2015 | Nakamura et al. |

FOREIGN PATENT DOCUMENTS

| | | |
|---|---|---|
| AU | 200014990 A1 | 8/2000 |
| CN | 1280509 A | 1/2001 |
| CN | 1161893 C | 12/2004 |
| CN | 1933859 A | 3/2007 |
| CN | 102625717 A | 8/2012 |
| CN | 102791301 A | 11/2012 |
| CN | 102858381 A | 1/2013 |
| CN | 104244999 A | 12/2014 |
| EP | 2543397 A1 | 1/2013 |
| JP | 2001-293081 A | 10/2001 |
| JP | 2001-519210 A | 10/2001 |
| JP | 2003-275294 A | 9/2003 |

(Continued)

OTHER PUBLICATIONS

Zhang et al., Crit Rev Biomed Eng. 2009; 27(1-2):1-57 (Year: 2009).*
Xiaobing et al., "Principles and Practice of Regenerative Medicine", 1st edition, Mar. 2008, pp. 584-585, English Translation (Year: 2008).*
Pettersson et al., "Biodegradable gelatin microcarriers in tissue engineering: In vitro studies on cartilage and bone", Dissertations No. 1147, 2009 (72 pages total).
Pulkkinen et al., "The use of recombinant human type II collagen for articular cartilage tissue engineering", Dissertation in Health Sciences, No. 142, 2012 (113 pages total).

(Continued)

*Primary Examiner* — Scott Long
*Assistant Examiner* — Evelyn Y Pyla
(74) *Attorney, Agent, or Firm* — Birch, Stewart, Kolasch & Birch, LLP

(57) ABSTRACT

An object of the invention is to provide a cartilage regenerative material that is capable of regenerating bone and cartilage using cells. Provided is a cartilage regenerative material including a cell construct, which includes biocompatible polymer blocks and stem cells, in which a plurality of the biocompatible polymer blocks are disposed in gaps between a plurality of the stem cells.

15 Claims, 10 Drawing Sheets

Specification includes a Sequence Listing.

(56) References Cited

FOREIGN PATENT DOCUMENTS

| | | |
|---|---|---|
| JP | 2004-501700 A | 1/2004 |
| JP | 2004-357694 A | 12/2004 |
| JP | 2005-152006 A | 6/2005 |
| JP | 2006-289062 A | 10/2006 |
| JP | 4122280 B2 | 7/2008 |
| JP | 2010-535602 A | 11/2010 |
| JP | 2014-12114 A | 1/2014 |
| JP | 2015-54887 A | 3/2015 |
| WO | WO 2006/022671 A1 | 3/2006 |
| WO | WO 2011/021712 A1 | 2/2011 |
| WO | WO 2011/108517 A1 | 9/2011 |
| WO | WO 2011/108537 A1 | 9/2011 |
| WO | WO 2014/133081 A1 | 9/2014 |

OTHER PUBLICATIONS

U.S. Non-Final Office Action dated Dec. 23, 2019, for U.S. Appl. No. 15/705,669.
Chinese Office Action and Search Report for corresponding Chinese Application No. 201680016000.8, dated Jan. 6, 2020, with English translation.
Chinese Office Action and Search Report, dated Nov. 13. 2019 for corresponding Chinese Application No. 201680016571.1, with an English translation of the Chinese Office Action..
Chinese Office Action for corresponding Chinese Application No. 201680016571.1, dated Jul. 30, 2020, with an English translation.
U.S. Office Action for U.S. Appl. No. 15/705,669, dated Jul. 27, 2020.
European Office Action for corresponding European Application No. 16765074.6, dated May 7, 2019.
Extended European Search Report for corresponding European Application No. 16765074.6, dated Feb. 14, 2018.
Extended European Search Report for corresponding European Application No. 16765075.3, dated Feb. 15, 2018.
Huang et al., "Solid freeform-fabricated scaffolds designed to carry multicellular mesenchymal stem cell spheroids for cartilage regeneration," European Cells and Materials, vol. 26, 2013, pp. 179-194.
International Preliminary Report on Patentability and Written Opinion of the International Searching Authority (Forms PCT/IB/373, PCT/IB/326 and PCT/ISA/237), dated Sep. 28, 2017, for International Application No. PCT/JP2016/058540, with an English translation of the Written Opinion.
International Preliminary Report on Patentability and Written Opinion of the International Searching Authority (Forms PCT/IB/373, PCT/IB/326 and PCT/ISA/237), dated Sep. 28, 2017, for International Application No. PCT/JP2016/058541, with an English translation of the Written Opinion.
International Search Report and English translation (Form PCT/ISA/210), dated Jun. 21, 2016, for International Application No. PCT/JP2016/058541.
International Search Report and English translation (Form PCT/ISA/210), dated Jun. 7, 2016, for International Application No. PCT/JP2016/058540.
Japanese Notification of Reasons for Refusal for Japanese Application No. 2017-506615, dated Apr. 24, 2018, with machine translation.
Japanese Office Action and English translation for Application No. 2017-506614, dated May 22, 2018.
Japanese Office Action, dated Oct. 16, 2018, for Japanese Application No. 2017-506615, with an English machine translation.
Lee et al., "Transplantation of scaffold-free spheroids composed of synovium-derived cells and chondrocytes for the treatment of cartilage defects of the knee," European Cells and Materials, vol. 22, 2011, pp. 275-290.
Ponticello et al., "Gelatin-Based Resorbable Spong as a Carrier Matrix for Human Mesenchymal Stem Cells in Cartilage Regeneration Therapy," J Biomed Mater Res, vol. 52, 2000, pp. 246-255.
Raghunath et al., "Advancing Cartilage Tissue Engineering: the Application of Stem Cell Technology," Current Opinions in Biotechnology, vol. 16, 2005 (published on web Sep. 8, 2005), pp. 503-509.
Toh et al., "Advances in mesenchymal stem cell-based strategies for cartilage repair and regeneration," Stem Cell Reviews and Reports, vol. 10, 2014 (published online May 29, 2014), pp. 686-696.
Yoshioka, "Recombinant collagen technology applying on regenerative medicine," Medical Science Digest, vol. 40, No. 12, 2014, pp. 46-49 (6 pages total).
U.S. Non-Final Office Action dated Jul. 22, 2019, dated for U.S. Appl. No. 15/705,826.
Chinese Office Action for counterpart Chinese Application No. 201680016000.8, dated Sep. 22, 2020, with English translation.
European Office Action for counterpart European Application No. 16765074.6, dated Aug. 27, 2020.
Chinese Office Action for Appl. No. 201680016000.8 dated Feb. 22, 2021.
Chinese Office Action for Appl. No. 201680016571.1 dated Feb. 22. 2021.
European Communication pursuant to Article 94(3) EPC for European Application No. 16765075.3. dated Oct. 26, 2020.
Chinese Office Action for corresponding Chinese Application No. 201680016000.8, dated May 27, 2021, with English translation.
Chinese Office Action and Search Report for Chinese Application No. 201680016571.1, dated Jul. 21, 2021, with an English translation.
Chinese Office Action for Appl. No. 201680016000.8 dated Nov. 9, 2021 (w/ English translation).
Xiaobing, F. et al., "Principles and Practice of Regenerative Medicine", 1st edition, Mar. 2008, pp. 584-585.

\* cited by examiner

SEQUENCE LISTING

```
<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: Synthetic: Recombinant

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
                20                  25                  30

Arg Gly Asp Ala Gly Pro Lys Gly Ala Asp Gly Ala Pro Gly Ala Pro
            35                  40                  45

Gly Leu Gln Gly Met Pro Gly Glu Arg Gly Ala Ala Gly Leu Pro Gly
        50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
                100                 105                 110

Asp Ala Gly Pro Lys Gly Ala Asp Gly Ala Pro Gly Lys Asp Gly Val
            115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
            260                 265                 270

Asp Gly Val Arg Gly Leu Ala Gly Pro Ile Gly Pro Pro Gly Glu Arg
        275                 280                 285

Gly Ala Ala Gly Leu Pro Gly Pro Lys Gly Glu Arg Gly Asp Ala Gly
    290                 295                 300
```

```
Pro Lys Gly Ala Asp Gly Ala Pro Lys Asp Gly Val Arg Gly Leu
305                 310                 315                 320

Ala Gly Pro Ile Gly Pro Pro Gly Pro Ala Gly Ala Pro Gly Ala Pro
            325                 330                 335

Gly Leu Gln Gly Met Pro Gly Glu Arg Gly Ala Ala Gly Leu Pro Gly
            340                 345                 350

Pro Lys Gly Glu Arg Gly Asp Ala Gly Pro Lys Gly Ala Asp Gly Ala
        355                 360                 365

Pro Gly Lys Asp Gly Val Arg Gly Leu Ala Gly Pro Pro Gly Ala Pro
        370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
                405                 410                 415

Lys Gly Ala Asp Gly Ala Pro Gly Ala Pro Gly Leu Gln Gly Met Pro
            420                 425                 430

Gly Glu Arg Gly Ala Ala Gly Leu Pro Gly Pro Lys Gly Glu Arg Gly
        435                 440                 445

Asp Ala Gly Pro Lys Gly Ala Asp Gly Ala Pro Gly Lys Asp Gly Val
450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
                485                 490                 495

Ala Asp Gly Ala Pro Gly Lys Asp Gly Val Arg Gly Leu Ala Gly Pro
            500                 505                 510

Ile Gly Pro Pro Gly Pro Ala Gly Ala Pro Gly Ala Pro Gly Leu Gln
        515                 520                 525

Gly Met Pro Gly Glu Arg Gly Ala Ala Gly Leu Pro Gly Pro Lys Gly
        530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Pro Gly
                565                 570

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 3

Tyr Ile Gly Ser Arg
1               5
```

```
<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: adhesive
      sequence
```

```
<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 10

Glu Arg Gly Asp
1

<210> SEQ ID NO 11
<211> LENGTH: 571
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
```

```
<220> FEATURE:
<221> NAME/KEY: misc_feature
<222> LOCATION: (44)..(45)
<223> OTHER INFORMATION: Xaa can be any naturally occurring amino acid
<220> FEATURE:
<221> NAME/KEY: misc_feature
<222> LOCATION: (47)..(48)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (59)..(60)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (65)..(66)
<223> OTHER INFORMATION: Xaa can be any naturally occurring amino acid
<220> FEATURE:
<221> NAME/KEY: misc_feature
<222> LOCATION: (68)..(69)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (74)..(75)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (83)..(84)
<223> OTHER INFORMATION: Xaa can be any naturally occurring amino acid
<220> FEATURE:
<221> NAME/KEY: misc_feature
<222> LOCATION: (86)..(87)
<223> OTHER INFORMATION: Xaa can be any naturally occurring amino acid
<220> FEATURE:
<221> NAME/KEY: misc_feature
<222> LOCATION: (89)..(90)
<223> OTHER INFORMATION: Xaa can be any naturally occurring amino acid
<220> FEATURE:
<221> NAME/KEY: misc_feature
<222> LOCATION: (92)..(93)
<223> OTHER INFORMATION: Xaa can be any naturally occurring amino acid
<220> FEATURE:
<221> NAME/KEY: misc_feature
<222> LOCATION: (95)..(96)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: misc_feature
<222> LOCATION: (101)..(102)
```

```
<223> OTHER INFORMATION: Xaa can be any naturally occurring amino acid
<220> FEATURE:
<221> NAME/KEY: misc_feature
<222> LOCATION: (104)..(105)
<223> OTHER INFORMATION: Xaa can be any naturally occurring amino acid
<220> FEATURE:
<221> NAME/KEY: misc_feature
<222> LOCATION: (107)..(108)
<223> OTHER INFORMATION: Xaa can be any naturally occurring amino acid
<220> FEATURE:
<221> NAME/KEY: misc_feature
<222> LOCATION: (110)..(111)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid
<220> FEATURE:
<221> NAME/KEY: misc_feature
<222> LOCATION: (116)..(117)
<223> OTHER INFORMATION: Xaa can be any naturally occurring amino acid
<220> FEATURE:
<221> NAME/KEY: misc_feature
<222> LOCATION: (119)..(120)
<223> OTHER INFORMATION: Xaa can be any naturally occurring amino acid
<220> FEATURE:
<221> NAME/KEY: misc_feature
<222> LOCATION: (122)..(123)
<223> OTHER INFORMATION: Xaa can be any naturally occurring amino acid
<220> FEATURE:
<221> NAME/KEY: misc_feature
<222> LOCATION: (125)..(126)
<223> OTHER INFORMATION: Xaa can be any naturally occurring amino acid
<220> FEATURE:
<221> NAME/KEY: misc_feature
<222> LOCATION: (128)..(129)
<223> OTHER INFORMATION: Xaa can be any naturally occurring amino acid
<220> FEATURE:
<221> NAME/KEY: misc_feature
<222> LOCATION: (131)..(132)
<223> OTHER INFORMATION: Xaa can be any naturally occurring amino acid
<220> FEATURE:
<221> NAME/KEY: misc_feature
<222> LOCATION: (134)..(135)
<223> OTHER INFORMATION: Xaa can be any naturally occurring amino acid
<220> FEATURE:
<221> NAME/KEY: misc_feature
<222> LOCATION: (137)..(138)
<223> OTHER INFORMATION: Xaa can be any naturally occurring amino acid
<220> FEATURE:
<221> NAME/KEY: misc_feature
<222> LOCATION: (140)..(141)
<223> OTHER INFORMATION: Xaa can be any naturally occurring amino acid
<220> FEATURE:
<221> NAME/KEY: misc_feature
<222> LOCATION: (143)..(144)
<223> OTHER INFORMATION: Xaa can be any naturally occurring amino acid
<220> FEATURE:
<221> NAME/KEY: misc_feature
<222> LOCATION: (146)..(147)
<223> OTHER INFORMATION: Xaa can be any naturally occurring amino acid
<220> FEATURE:
<221> NAME/KEY: misc_feature
<222> LOCATION: (149)..(150)
<223> OTHER INFORMATION: Xaa can be any naturally occurring amino acid
<220> FEATURE:
<221> NAME/KEY: misc_feature
<222> LOCATION: (152)..(153)
<223> OTHER INFORMATION: Xaa can be any naturally occurring amino acid
<220> FEATURE:
<221> NAME/KEY: misc_feature
<222> LOCATION: (155)..(156)
<223> OTHER INFORMATION: Xaa can be any naturally occurring amino acid
<220> FEATURE:
<221> NAME/KEY: misc_feature
<222> LOCATION: (158)..(159)
<223> OTHER INFORMATION: Xaa can be any naturally occurring amino acid
<220> FEATURE:
<221> NAME/KEY: misc_feature
```

```
<222> LOCATION: (161)..(162)
<223> OTHER INFORMATION: Xaa can be any naturally occurring amino acid
<220> FEATURE:
<221> NAME/KEY: misc_feature
<222> LOCATION: (164)..(165)
<223> OTHER INFORMATION: Xaa can be any naturally occurring amino acid
<220> FEATURE:
<221> NAME/KEY: misc_feature
<222> LOCATION: (167)..(168)
<223> OTHER INFORMATION: Xaa can be any naturally occurring amino acid
<220> FEATURE:
<221> NAME/KEY: misc_feature
<222> LOCATION: (170)..(171)
<223> OTHER INFORMATION: Xaa can be any naturally occurring amino acid
<220> FEATURE:
<221> NAME/KEY: misc_feature
<222> LOCATION: (173)..(174)
<223> OTHER INFORMATION: Xaa can be any naturally occurring amino acid
<220> FEATURE:
<221> NAME/KEY: misc_feature
<222> LOCATION: (176)..(177)
<223> OTHER INFORMATION: Xaa can be any naturally occurring amino acid
<220> FEATURE:
<221> NAME/KEY: misc_feature
<222> LOCATION: (179)..(180)
<223> OTHER INFORMATION: Xaa can be any naturally occurring amino acid
<220> FEATURE:
<221> NAME/KEY: misc_feature
<222> LOCATION: (182)..(183)
<223> OTHER INFORMATION: Xaa can be any naturally occurring amino acid
<220> FEATURE:
<221> NAME/KEY: misc_feature
<222> LOCATION: (185)..(186)
<223> OTHER INFORMATION: Xaa can be any naturally occurring amino acid
<220> FEATURE:
<221> NAME/KEY: misc_feature
<222> LOCATION: (188)..(189)
<223> OTHER INFORMATION: Xaa can be any naturally occurring amino acid
<220> FEATURE:
<221> NAME/KEY: misc_feature
<222> LOCATION: (191)..(192)
<223> OTHER INFORMATION: Xaa can be any naturally occurring amino acid
<220> FEATURE:
<221> NAME/KEY: misc_feature
<222> LOCATION: (194)..(195)
<223> OTHER INFORMATION: Xaa can be any naturally occurring amino acid
<220> FEATURE:
<221> NAME/KEY: misc_feature
<222> LOCATION: (197)..(198)
<223> OTHER INFORMATION: Xaa can be any naturally occurring amino acid
<220> FEATURE:
<221> NAME/KEY: misc_feature
<222> LOCATION: (200)..(201)
<223> OTHER INFORMATION: Xaa can be any naturally occurring amino acid
<220> FEATURE:
<221> NAME/KEY: misc_feature
<222> LOCATION: (203)..(204)
<223> OTHER INFORMATION: Xaa can be any naturally occurring amino acid
<220> FEATURE:
<221> NAME/KEY: misc_feature
<222> LOCATION: (206)..(207)
<223> OTHER INFORMATION: Xaa can be any naturally occurring amino acid
<220> FEATURE:
<221> NAME/KEY: misc_feature
<222> LOCATION: (209)..(210)
<223> OTHER INFORMATION: Xaa can be any naturally occurring amino acid
<220> FEATURE:
<221> NAME/KEY: misc_feature
<222> LOCATION: (212)..(213)
<223> OTHER INFORMATION: Xaa can be any naturally occurring amino acid
<220> FEATURE:
<221> NAME/KEY: misc_feature
<222> LOCATION: (215)..(216)
<223> OTHER INFORMATION: Xaa can be any naturally occurring amino acid
<220> FEATURE:
<221> NAME/KEY: misc_feature
<222> LOCATION: (218)..(219)
<223> OTHER INFORMATION: Xaa can be any naturally occurring amino acid
<220> FEATURE:
```

```
<221> NAME/KEY: misc_feature
<222> LOCATION: (221)..(222)
<223> OTHER INFORMATION: Xaa can be any naturally occurring amino acid
<220> FEATURE:
<221> NAME/KEY: misc_feature
<222> LOCATION: (224)..(225)
<223> OTHER INFORMATION: Xaa can be any naturally occurring amino acid
<220> FEATURE:
<221> NAME/KEY: misc_feature
<222> LOCATION: (227)..(228)
<223> OTHER INFORMATION: Xaa can be any naturally occurring amino acid
<220> FEATURE:
<221> NAME/KEY: misc_feature
<222> LOCATION: (230)..(231)
<223> OTHER INFORMATION: Xaa can be any naturally occurring amino acid
<220> FEATURE:
<221> NAME/KEY: misc_feature
<222> LOCATION: (233)..(234)
<223> OTHER INFORMATION: Xaa can be any naturally occurring amino acid
<220> FEATURE:
<221> NAME/KEY: misc_feature
<222> LOCATION: (236)..(237)
<223> OTHER INFORMATION: Xaa can be any naturally occurring amino acid
<220> FEATURE:
<221> NAME/KEY: misc_feature
<222> LOCATION: (239)..(240)
<223> OTHER INFORMATION: Xaa can be any naturally occurring amino acid
<220> FEATURE:
<221> NAME/KEY: misc_feature
<222> LOCATION: (242)..(243)
<223> OTHER INFORMATION: Xaa can be any naturally occurring amino acid
<220> FEATURE:
<221> NAME/KEY: misc_feature
<222> LOCATION: (245)..(246)
<223> OTHER INFORMATION: Xaa can be any naturally occurring amino acid
<220> FEATURE:
<221> NAME/KEY: misc_feature
<222> LOCATION: (248)..(249)
<223> OTHER INFORMATION: Xaa can be any naturally occurring amino acid
<220> FEATURE:
<221> NAME/KEY: misc_feature
<222> LOCATION: (251)..(252)
<223> OTHER INFORMATION: Xaa can be any naturally occurring amino acid
<220> FEATURE:
<221> NAME/KEY: misc_feature
<222> LOCATION: (254)..(255)
<223> OTHER INFORMATION: Xaa can be any naturally occurring amino acid
<220> FEATURE:
<221> NAME/KEY: misc_feature
<222> LOCATION: (257)..(258)
<223> OTHER INFORMATION: Xaa can be any naturally occurring amino acid
<220> FEATURE:
<221> NAME/KEY: misc_feature
<222> LOCATION: (260)..(261)
<223> OTHER INFORMATION: Xaa can be any naturally occurring amino acid
<220> FEATURE:
<221> NAME/KEY: misc_feature
<222> LOCATION: (263)..(264)
<223> OTHER INFORMATION: Xaa can be any naturally occurring amino acid
<220> FEATURE:
<221> NAME/KEY: misc_feature
<222> LOCATION: (266)..(267)
<223> OTHER INFORMATION: Xaa can be any naturally occurring amino acid
<220> FEATURE:
<221> NAME/KEY: misc_feature
<222> LOCATION: (269)..(270)
<223> OTHER INFORMATION: Xaa can be any naturally occurring amino acid
<220> FEATURE:
<221> NAME/KEY: misc_feature
<222> LOCATION: (272)..(273)
<223> OTHER INFORMATION: Xaa can be any naturally occurring amino acid
<220> FEATURE:
<221> NAME/KEY: misc_feature
<222> LOCATION: (275)..(276)
<223> OTHER INFORMATION: Xaa can be any naturally occurring amino acid
<220> FEATURE:
<221> NAME/KEY: misc_feature
<222> LOCATION: (278)..(279)
<223> OTHER INFORMATION: Xaa can be any naturally occurring amino acid
```

```
<220> FEATURE:
<221> NAME/KEY: misc_feature
<222> LOCATION: (281)..(282)
<223> OTHER INFORMATION: Xaa can be any naturally occurring amino acid
<220> FEATURE:
<221> NAME/KEY: misc_feature
<222> LOCATION: (284)..(285)
<223> OTHER INFORMATION: Xaa can be any naturally occurring amino acid
<220> FEATURE:
<221> NAME/KEY: misc_feature
<222> LOCATION: (287)..(288)
<223> OTHER INFORMATION: Xaa can be any naturally occurring amino acid
<220> FEATURE:
<221> NAME/KEY: misc_feature
<222> LOCATION: (290)..(291)
<223> OTHER INFORMATION: Xaa can be any naturally occurring amino acid
<220> FEATURE:
<221> NAME/KEY: misc_feature
<222> LOCATION: (293)..(294)
<223> OTHER INFORMATION: Xaa can be any naturally occurring amino acid
<220> FEATURE:
<221> NAME/KEY: misc_feature
<222> LOCATION: (296)..(297)
<223> OTHER INFORMATION: Xaa can be any naturally occurring amino acid
<220> FEATURE:
<221> NAME/KEY: misc_feature
<222> LOCATION: (299)..(300)
<223> OTHER INFORMATION: Xaa can be any naturally occurring amino acid
<220> FEATURE:
<221> NAME/KEY: misc_feature
<222> LOCATION: (302)..(303)
<223> OTHER INFORMATION: Xaa can be any naturally occurring amino acid
<220> FEATURE:
<221> NAME/KEY: misc_feature
<222> LOCATION: (305)..(306)
<223> OTHER INFORMATION: Xaa can be any naturally occurring amino acid
<220> FEATURE:
<221> NAME/KEY: misc_feature
<222> LOCATION: (308)..(309)
<223> OTHER INFORMATION: Xaa can be any naturally occurring amino acid
<220> FEATURE:
<221> NAME/KEY: misc_feature
<222> LOCATION: (311)..(312)
<223> OTHER INFORMATION: Xaa can be any naturally occurring amino acid
<220> FEATURE:
<221> NAME/KEY: misc_feature
<222> LOCATION: (314)..(315)
<223> OTHER INFORMATION: Xaa can be any naturally occurring amino acid
<220> FEATURE:
<221> NAME/KEY: misc_feature
<222> LOCATION: (317)..(318)
<223> OTHER INFORMATION: Xaa can be any naturally occurring amino acid
<220> FEATURE:
<221> NAME/KEY: misc_feature
<222> LOCATION: (320)..(321)
<223> OTHER INFORMATION: Xaa can be any naturally occurring amino acid
<220> FEATURE:
<221> NAME/KEY: misc_feature
<222> LOCATION: (323)..(324)
<223> OTHER INFORMATION: Xaa can be any naturally occurring amino acid
<220> FEATURE:
<221> NAME/KEY: misc_feature
<222> LOCATION: (326)..(327)
<223> OTHER INFORMATION: Xaa can be any naturally occurring amino acid
<220> FEATURE:
<221> NAME/KEY: misc_feature
<222> LOCATION: (329)..(330)
<223> OTHER INFORMATION: Xaa can be any naturally occurring amino acid
<220> FEATURE:
<221> NAME/KEY: misc_feature
<222> LOCATION: (332)..(333)
<223> OTHER INFORMATION: Xaa can be any naturally occurring amino acid
<220> FEATURE:
<221> NAME/KEY: misc_feature
<222> LOCATION: (335)..(336)
<223> OTHER INFORMATION: Xaa can be any naturally occurring amino acid
<220> FEATURE:
<221> NAME/KEY: misc_feature
<222> LOCATION: (338)..(339)
```

```
<223> OTHER INFORMATION: Xaa can be any naturally occurring amino acid
<220> FEATURE:
<221> NAME/KEY: misc_feature
<222> LOCATION: (341)..(342)
<223> OTHER INFORMATION: Xaa can be any naturally occurring amino acid
<220> FEATURE:
<221> NAME/KEY: misc_feature
<222> LOCATION: (344)..(345)
<223> OTHER INFORMATION: Xaa can be any naturally occurring amino acid
<220> FEATURE:
<221> NAME/KEY: misc_feature
<222> LOCATION: (347)..(348)
<223> OTHER INFORMATION: Xaa can be any naturally occurring amino acid
<220> FEATURE:
<221> NAME/KEY: misc_feature
<222> LOCATION: (350)..(351)
<223> OTHER INFORMATION: Xaa can be any naturally occurring amino acid
<220> FEATURE:
<221> NAME/KEY: misc_feature
<222> LOCATION: (353)..(354)
<223> OTHER INFORMATION: Xaa can be any naturally occurring amino acid
<220> FEATURE:
<221> NAME/KEY: misc_feature
<222> LOCATION: (356)..(357)
<223> OTHER INFORMATION: Xaa can be any naturally occurring amino acid
<220> FEATURE:
<221> NAME/KEY: misc_feature
<222> LOCATION: (359)..(360)
<223> OTHER INFORMATION: Xaa can be any naturally occurring amino acid
<220> FEATURE:
<221> NAME/KEY: misc_feature
<222> LOCATION: (362)..(363)
<223> OTHER INFORMATION: Xaa can be any naturally occurring amino acid
<220> FEATURE:
<221> NAME/KEY: misc_feature
<222> LOCATION: (365)..(366)
<223> OTHER INFORMATION: Xaa can be any naturally occurring amino acid
<220> FEATURE:
<221> NAME/KEY: misc_feature
<222> LOCATION: (368)..(369)
<223> OTHER INFORMATION: Xaa can be any naturally occurring amino acid
<220> FEATURE:
<221> NAME/KEY: misc_feature
<222> LOCATION: (371)..(372)
<223> OTHER INFORMATION: Xaa can be any naturally occurring amino acid
<220> FEATURE:
<221> NAME/KEY: misc_feature
<222> LOCATION: (374)..(375)
<223> OTHER INFORMATION: Xaa can be any naturally occurring amino acid
<220> FEATURE:
<221> NAME/KEY: misc_feature
<222> LOCATION: (377)..(378)
<223> OTHER INFORMATION: Xaa can be any naturally occurring amino acid
<220> FEATURE:
<221> NAME/KEY: misc_feature
<222> LOCATION: (380)..(381)
<223> OTHER INFORMATION: Xaa can be any naturally occurring amino acid
<220> FEATURE:
<221> NAME/KEY: misc_feature
<222> LOCATION: (383)..(384)
<223> OTHER INFORMATION: Xaa can be any naturally occurring amino acid
<220> FEATURE:
<221> NAME/KEY: misc_feature
<222> LOCATION: (386)..(387)
<223> OTHER INFORMATION: Xaa can be any naturally occurring amino acid
<220> FEATURE:
<221> NAME/KEY: misc_feature
<222> LOCATION: (389)..(390)
<223> OTHER INFORMATION: Xaa can be any naturally occurring amino acid
<220> FEATURE:
<221> NAME/KEY: misc_feature
<222> LOCATION: (392)..(393)
<223> OTHER INFORMATION: Xaa can be any naturally occurring amino acid
<220> FEATURE:
<221> NAME/KEY: misc_feature
<222> LOCATION: (395)..(396)
<223> OTHER INFORMATION: Xaa can be any naturally occurring amino acid
<220> FEATURE:
<221> NAME/KEY: misc_feature
```

```
<222> LOCATION: (398)..(399)
<223> OTHER INFORMATION: Xaa can be any naturally occurring amino acid
<220> FEATURE:
<221> NAME/KEY: misc_feature
<222> LOCATION: (401)..(402)
<223> OTHER INFORMATION: Xaa can be any naturally occurring amino acid
<220> FEATURE:
<221> NAME/KEY: misc_feature
<222> LOCATION: (404)..(405)
<223> OTHER INFORMATION: Xaa can be any naturally occurring amino acid
<220> FEATURE:
<221> NAME/KEY: misc_feature
<222> LOCATION: (407)..(408)
<223> OTHER INFORMATION: Xaa can be any naturally occurring amino acid
<220> FEATURE:
<221> NAME/KEY: misc_feature
<222> LOCATION: (410)..(411)
<223> OTHER INFORMATION: Xaa can be any naturally occurring amino acid
<220> FEATURE:
<221> NAME/KEY: misc_feature
<222> LOCATION: (413)..(414)
<223> OTHER INFORMATION: Xaa can be any naturally occurring amino acid
<220> FEATURE:
<221> NAME/KEY: misc_feature
<222> LOCATION: (416)..(417)
<223> OTHER INFORMATION: Xaa can be any naturally occurring amino acid
<220> FEATURE:
<221> NAME/KEY: misc_feature
<222> LOCATION: (419)..(420)
<223> OTHER INFORMATION: Xaa can be any naturally occurring amino acid
<220> FEATURE:
<221> NAME/KEY: misc_feature
<222> LOCATION: (422)..(423)
<223> OTHER INFORMATION: Xaa can be any naturally occurring amino acid
<220> FEATURE:
<221> NAME/KEY: misc_feature
<222> LOCATION: (425)..(426)
<223> OTHER INFORMATION: Xaa can be any naturally occurring amino acid
<220> FEATURE:
<221> NAME/KEY: misc_feature
<222> LOCATION: (428)..(429)
<223> OTHER INFORMATION: Xaa can be any naturally occurring amino acid
<220> FEATURE:
<221> NAME/KEY: misc_feature
<222> LOCATION: (431)..(432)
<223> OTHER INFORMATION: Xaa can be any naturally occurring amino acid
<220> FEATURE:
<221> NAME/KEY: misc_feature
<222> LOCATION: (434)..(435)
<223> OTHER INFORMATION: Xaa can be any naturally occurring amino acid
<220> FEATURE:
<221> NAME/KEY: misc_feature
<222> LOCATION: (437)..(438)
<223> OTHER INFORMATION: Xaa can be any naturally occurring amino acid
<220> FEATURE:
<221> NAME/KEY: misc_feature
<222> LOCATION: (440)..(441)
<223> OTHER INFORMATION: Xaa can be any naturally occurring amino acid
<220> FEATURE:
<221> NAME/KEY: misc_feature
<222> LOCATION: (443)..(444)
<223> OTHER INFORMATION: Xaa can be any naturally occurring amino acid
<220> FEATURE:
<221> NAME/KEY: misc_feature
<222> LOCATION: (446)..(447)
<223> OTHER INFORMATION: Xaa can be any naturally occurring amino acid
<220> FEATURE:
<221> NAME/KEY: misc_feature
<222> LOCATION: (449)..(450)
<223> OTHER INFORMATION: Xaa can be any naturally occurring amino acid
<220> FEATURE:
<221> NAME/KEY: misc_feature
<222> LOCATION: (452)..(453)
<223> OTHER INFORMATION: Xaa can be any naturally occurring amino acid
<220> FEATURE:
<221> NAME/KEY: misc_feature
<222> LOCATION: (455)..(456)
<223> OTHER INFORMATION: Xaa can be any naturally occurring amino acid
<220> FEATURE:
```

```
<221> NAME/KEY: misc_feature
<222> LOCATION: (458)..(459)
<223> OTHER INFORMATION: Xaa can be any naturally occurring amino acid
<220> FEATURE:
<221> NAME/KEY: misc_feature
<222> LOCATION: (461)..(462)
<223> OTHER INFORMATION: Xaa can be any naturally occurring amino acid
<220> FEATURE:
<221> NAME/KEY: misc_feature
<222> LOCATION: (464)..(465)
<223> OTHER INFORMATION: Xaa can be any naturally occurring amino acid
<220> FEATURE:
<221> NAME/KEY: misc_feature
<222> LOCATION: (467)..(468)
<223> OTHER INFORMATION: Xaa can be any naturally occurring amino acid
<220> FEATURE:
<221> NAME/KEY: misc_feature
<222> LOCATION: (470)..(471)
<223> OTHER INFORMATION: Xaa can be any naturally occurring amino acid
<220> FEATURE:
<221> NAME/KEY: misc_feature
<222> LOCATION: (473)..(474)
<223> OTHER INFORMATION: Xaa can be any naturally occurring amino acid
<220> FEATURE:
<221> NAME/KEY: misc_feature
<222> LOCATION: (476)..(477)
<223> OTHER INFORMATION: Xaa can be any naturally occurring amino acid
<220> FEATURE:
<221> NAME/KEY: misc_feature
<222> LOCATION: (479)..(480)
<223> OTHER INFORMATION: Xaa can be any naturally occurring amino acid
<220> FEATURE:
<221> NAME/KEY: misc_feature
<222> LOCATION: (482)..(483)
<223> OTHER INFORMATION: Xaa can be any naturally occurring amino acid
<220> FEATURE:
<221> NAME/KEY: misc_feature
<222> LOCATION: (485)..(486)
<223> OTHER INFORMATION: Xaa can be any naturally occurring amino acid
<220> FEATURE:
<221> NAME/KEY: misc_feature
<222> LOCATION: (488)..(489)
<223> OTHER INFORMATION: Xaa can be any naturally occurring amino acid
<220> FEATURE:
<221> NAME/KEY: misc_feature
<222> LOCATION: (491)..(492)
<223> OTHER INFORMATION: Xaa can be any naturally occurring amino acid
<220> FEATURE:
<221> NAME/KEY: misc_feature
<222> LOCATION: (494)..(495)
<223> OTHER INFORMATION: Xaa can be any naturally occurring amino acid
<220> FEATURE:
<221> NAME/KEY: misc_feature
<222> LOCATION: (497)..(498)
<223> OTHER INFORMATION: Xaa can be any naturally occurring amino acid
<220> FEATURE:
<221> NAME/KEY: misc_feature
<222> LOCATION: (500)..(501)
<223> OTHER INFORMATION: Xaa can be any naturally occurring amino acid
<220> FEATURE:
<221> NAME/KEY: misc_feature
<222> LOCATION: (503)..(504)
<223> OTHER INFORMATION: Xaa can be any naturally occurring amino acid
<220> FEATURE:
<221> NAME/KEY: misc_feature
<222> LOCATION: (506)..(507)
<223> OTHER INFORMATION: Xaa can be any naturally occurring amino acid
<220> FEATURE:
<221> NAME/KEY: misc_feature
<222> LOCATION: (509)..(510)
<223> OTHER INFORMATION: Xaa can be any naturally occurring amino acid
<220> FEATURE:
<221> NAME/KEY: misc_feature
<222> LOCATION: (512)..(513)
<223> OTHER INFORMATION: Xaa can be any naturally occurring amino acid
<220> FEATURE:
<221> NAME/KEY: misc_feature
<222> LOCATION: (515)..(516)
<223> OTHER INFORMATION: Xaa can be any naturally occurring amino acid
```

```
<220> FEATURE:
<221> NAME/KEY: misc_feature
<222> LOCATION: (518)..(519)
<223> OTHER INFORMATION: Xaa can be any naturally occurring amino acid
<220> FEATURE:
<221> NAME/KEY: misc_feature
<222> LOCATION: (521)..(522)
<223> OTHER INFORMATION: Xaa can be any naturally occurring amino acid
<220> FEATURE:
<221> NAME/KEY: misc_feature
<222> LOCATION: (524)..(525)
<223> OTHER INFORMATION: Xaa can be any naturally occurring amino acid
<220> FEATURE:
<221> NAME/KEY: misc_feature
<222> LOCATION: (527)..(528)
<223> OTHER INFORMATION: Xaa can be any naturally occurring amino acid
<220> FEATURE:
<221> NAME/KEY: misc_feature
<222> LOCATION: (530)..(531)
<223> OTHER INFORMATION: Xaa can be any naturally occurring amino acid
<220> FEATURE:
<221> NAME/KEY: misc_feature
<222> LOCATION: (533)..(534)
<223> OTHER INFORMATION: Xaa can be any naturally occurring amino acid
<220> FEATURE:
<221> NAME/KEY: misc_feature
<222> LOCATION: (536)..(537)
<223> OTHER INFORMATION: Xaa can be any naturally occurring amino acid
<220> FEATURE:
<221> NAME/KEY: misc_feature
<222> LOCATION: (539)..(540)
<223> OTHER INFORMATION: Xaa can be any naturally occurring amino acid
<220> FEATURE:
<221> NAME/KEY: misc_feature
<222> LOCATION: (542)..(543)
<223> OTHER INFORMATION: Xaa can be any naturally occurring amino acid
<220> FEATURE:
<221> NAME/KEY: misc_feature
<222> LOCATION: (545)..(546)
<223> OTHER INFORMATION: Xaa can be any naturally occurring amino acid
<220> FEATURE:
<221> NAME/KEY: misc_feature
<222> LOCATION: (548)..(549)
<223> OTHER INFORMATION: Xaa can be any naturally occurring amino acid
<220> FEATURE:
<221> NAME/KEY: misc_feature
<222> LOCATION: (551)..(552)
<223> OTHER INFORMATION: Xaa can be any naturally occurring amino acid
<220> FEATURE:
<221> NAME/KEY: misc_feature
<222> LOCATION: (554)..(555)
<223> OTHER INFORMATION: Xaa can be any naturally occurring amino acid
<220> FEATURE:
<221> NAME/KEY: misc_feature
<222> LOCATION: (557)..(558)
<223> OTHER INFORMATION: Xaa can be any naturally occurring amino acid
<220> FEATURE:
<221> NAME/KEY: misc_feature
<222> LOCATION: (560)..(561)
<223> OTHER INFORMATION: Xaa can be any naturally occurring amino acid
<220> FEATURE:
<221> NAME/KEY: misc_feature
<222> LOCATION: (563)..(564)
<223> OTHER INFORMATION: Xaa can be any naturally occurring amino acid
<220> FEATURE:
<221> NAME/KEY: misc_feature
<222> LOCATION: (566)..(567)
<223> OTHER INFORMATION: Xaa can be any naturally occurring amino acid
<220> FEATURE:
<221> NAME/KEY: misc_feature
<222> LOCATION: (569)..(570)
<223> OTHER INFORMATION: Xaa can be any naturally occurring amino acid

<400> SEQUENCE: 11

Gly Ala Pro Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
```

```
                20                  25                  30
Xaa Gly Xaa Xaa Gly Xaa Xaa Gly Xaa Xaa Gly Xaa Xaa Gly Xaa Xaa
            35                  40                  45
Gly Xaa Xaa Gly Xaa Xaa Gly Xaa Xaa Gly Xaa Xaa Gly Xaa Xaa Gly
        50                  55                  60
Xaa Xaa Gly Xaa Xaa Gly Xaa Xaa Gly Xaa Xaa Gly Xaa Xaa Gly Xaa
65                  70                  75                  80
Xaa Gly Xaa Xaa Gly Xaa Xaa Gly Xaa Xaa Gly Xaa Xaa Gly Xaa Xaa
            85                  90                  95
Gly Xaa Xaa Gly Xaa Xaa Gly Xaa Xaa Gly Xaa Xaa Gly Xaa Xaa Gly
        100                 105                 110
Xaa Xaa Gly Xaa Xaa Gly Xaa Xaa Gly Xaa Xaa Gly Xaa Xaa Gly Xaa
        115                 120                 125
Xaa Gly Xaa Xaa Gly Xaa Xaa Gly Xaa Xaa Gly Xaa Xaa Gly Xaa Xaa
        130                 135                 140
Gly Xaa Xaa Gly Xaa Xaa Gly Xaa Xaa Gly Xaa Xaa Gly Xaa Xaa Gly
145                 150                 155                 160
Xaa Xaa Gly Xaa Xaa Gly Xaa Xaa Gly Xaa Xaa Gly Xaa Xaa Gly Xaa
        165                 170                 175
Xaa Gly Xaa Xaa Gly Xaa Xaa Gly Xaa Xaa Gly Xaa Xaa Gly Xaa Xaa
        180                 185                 190
Gly Xaa Xaa Gly Xaa Xaa Gly Xaa Xaa Gly Xaa Xaa Gly Xaa Xaa Gly
        195                 200                 205
Xaa Xaa Gly Xaa Xaa Gly Xaa Xaa Gly Xaa Xaa Gly Xaa Xaa Gly Xaa
        210                 215                 220
Xaa Gly Xaa Xaa Gly Xaa Xaa Gly Xaa Xaa Gly Xaa Xaa Gly Xaa Xaa
225                 230                 235                 240
Gly Xaa Xaa Gly Xaa Xaa Gly Xaa Xaa Gly Xaa Xaa Gly Xaa Xaa Gly
        245                 250                 255
Xaa Xaa Gly Xaa Xaa Gly Xaa Xaa Gly Xaa Xaa Gly Xaa Xaa Gly Xaa
        260                 265                 270
Xaa Gly Xaa Xaa Gly Xaa Xaa Gly Xaa Xaa Gly Xaa Xaa Gly Xaa Xaa
        275                 280                 285
Gly Xaa Xaa Gly Xaa Xaa Gly Xaa Xaa Gly Xaa Xaa Gly Xaa Xaa Gly
        290                 295                 300
Xaa Xaa Gly Xaa Xaa Gly Xaa Xaa Gly Xaa Xaa Gly Xaa Xaa Gly Xaa
305                 310                 315                 320
Xaa Gly Xaa Xaa Gly Xaa Xaa Gly Xaa Xaa Gly Xaa Xaa Gly Xaa Xaa
        325                 330                 335
Gly Xaa Xaa Gly Xaa Xaa Gly Xaa Xaa Gly Xaa Xaa Gly Xaa Xaa Gly
        340                 345                 350
Xaa Xaa Gly Xaa Xaa Gly Xaa Xaa Gly Xaa Xaa Gly Xaa Xaa Gly Xaa
        355                 360                 365
Xaa Gly Xaa Xaa Gly Xaa Xaa Gly Xaa Xaa Gly Xaa Xaa Gly Xaa Xaa
        370                 375                 380
Gly Xaa Xaa Gly Xaa Xaa Gly Xaa Xaa Gly Xaa Xaa Gly Xaa Xaa Gly
385                 390                 395                 400
Xaa Xaa Gly Xaa Xaa Gly Xaa Xaa Gly Xaa Xaa Gly Xaa Xaa Gly Xaa
        405                 410                 415
Xaa Gly Xaa Xaa Gly Xaa Xaa Gly Xaa Xaa Gly Xaa Xaa Gly Xaa Xaa
        420                 425                 430
Gly Xaa Xaa Gly Xaa Xaa Gly Xaa Xaa Gly Xaa Xaa Gly Xaa Xaa Gly
        435                 440                 445
```

```
Xaa Xaa Gly Xaa Xaa Gly Xaa Xaa Gly Xaa Xaa Gly Xaa Xaa Gly Xaa
        450             455             460

Xaa Gly Xaa Xaa Gly Xaa Xaa Gly Xaa Xaa Gly Xaa Xaa Gly Xaa Xaa
465             470             475             480

Gly Xaa Xaa Gly Xaa Xaa Gly Xaa Xaa Gly Xaa Xaa Gly Xaa Xaa Gly
            485             490             495

Xaa Xaa Gly Xaa Xaa Gly Xaa Xaa Gly Xaa Xaa Gly Xaa Xaa Gly Xaa
        500             505             510

Xaa Gly Xaa Xaa Gly Xaa Xaa Gly Xaa Xaa Gly Xaa Xaa
    515             520             525

Gly Xaa Xaa Gly Xaa Xaa Gly Xaa Xaa Gly Xaa Xaa Gly Xaa Xaa Gly
        530             535             540

Xaa Xaa Gly Xaa Xaa Gly Xaa Xaa Gly Xaa Xaa Gly Xaa Xaa Gly Xaa
545             550             555             560

Xaa Gly Xaa Xaa Gly Xaa Xaa Gly Xaa Xaa Gly
            565             570
```

CARTILAGE REGENERATIVE MATERIAL

CROSS-REFERENCE TO RELATED APPLICATIONS

This application is a Divisional of Ser. No. 15/705,826 filed on Sep. 15, 2017, which is a Continuation of PCT International Application No. PCT/JP2016/058540 filed on Mar. 17, 2016, which claims priority under 35 U.S.C § 119(a) to Japanese Patent Application No. 2015-054874 filed on Mar. 18, 2015. Each of the above application(s) is hereby expressly incorporated by reference, in its entirety, into the present application.

REFERENCE TO SEQUENCE LISTING SUBMITTED VIA EFS-WEB

This application includes an electronically submitted sequence listing in .txt format. The .txt file contains a sequence listing entitled "2017-11-16_2870-0673PUS1_ST25.txt" created on Nov. 16, 2017 and is 31,850 bytes in size. The sequence listing contained in this .txt file is part of the specification and is hereby incorporated by reference herein in its entirety.

BACKGROUND OF THE INVENTION

1. Field of the Invention

The present invention relates to a cartilage regenerative material including a cell construct that includes biocompatible polymer blocks and stem cells.

2. Description of the Related Art

Generally, articular osteochondral defects are not likely to be accompanied by spontaneous regeneration, and thus, regenerative medicine based on cell transplantation therapy has been actively attempted. Cell transplantation therapy has been attempted in many cases by administering cells in the form of cell aggregates. For example, it is described in JP4122280B that a tissue plug is produced by introducing a cell mass of cells derived from a tissue collected from a test animal or a patient into a chamber having micropores through which culture fluid can pass; and culturing the cell mass in an excess amount of culture fluid compared to the amount of the culture fluid in the chamber by introducing the culture fluid into the chamber in an amount such that a portion of the cell mass is in contact with the gas phase, and the tissue plug thus produced is transplanted. It is described in J. I. Lee, "Transplantation of scaffold-free spheroids composed of synovium-derived cells and chondrocytes or the treatment of cartilage defects of the knee," *European Cells and Materials*, Vol. 22, 2011, p 275-290, that spheroids that are composed of synovium-derived cells and chondrocytes and do not include a scaffold are transplanted for the treatment of knee cartilage loss.

Meanwhile, WO2011/108517A describes a cell construct that includes polymer blocks having biocompatibility and cells, in which a plurality of the polymer blocks are disposed in gaps between a plurality of the cells. In regard to the cell construct described in WO2011/108517A, delivery of nutrients from the outside to the inside of the cell construct is enabled, the cell construct has a sufficient thickness, and cells are uniformly distributed within the construct. In the Examples of JP4122280B, high cell survival activity was verified by using polymer blocks formed from a recombinant gelatin or naturally occurring gelatin material. In Example 11 of WO2011/108517A, it is described that the cell construct thus produced produces a large amount of glycosaminoglycan (GAG) and promotes chondrocyte differentiation.

SUMMARY OF THE INVENTION

As described above, regenerative medicine based on cell transplantation therapy has been attempted for articular osteochondral defects; however, simple administration of cells does not lead to engraftment of the cells onto the site of loss, and a sufficient regeneration effect is not obtained. Therefore, administration of cells in the form of cell aggregates has been attempted on numerous occasions (JP4122280B; J. I. Lee, "Transplantation of scaffold-free spheroids composed of synovium-derived cells and chondrocytes or the treatment of cartilage defects of the knee," *European Cells and Materials*, Vol. 22, 2011, p 275-290; and the like). However, even in a case in which cells are administered in the form of cell aggregates, it is difficult to simultaneously regenerate desired bone and cartilage while preventing the penetration of fibrous soft tissue. Also, it is described in WO2011/108517A that the cell construct produces a large amount of glycosaminoglycan (GAG); however, it has not been verified whether cartilage and bone can be regenerated simultaneously. In a case in which regenerative therapy for osteochondral defects is performed using cell aggregates as described above, the effects of regenerative therapy and the like are enhanced compared to the case of using isolated single cells; however, the effects are not necessarily satisfactory. Thus, there is a demand for a cell construct that exhibits a superior osteochondral regeneration effect.

It is an object of the invention to provide a cartilage regenerative material that can regenerate bone and cartilage using cells.

The inventors of the present invention conducted a thorough investigation in order to solve the problems described above, and as a result, the inventors found that a cell construct including biocompatible polymer blocks and stem cells, in which a plurality of the biocompatible polymer blocks are disposed in gaps between a plurality of the stem cells, has excellent cartilage regenerative capacity and excellent bone regenerative capacity. Thus, this invention was completed based on these findings.

That is, according to the invention, the following inventions are provided.

(1) A cartilage regenerative material comprising a cell construct that includes biocompatible polymer blocks and stem cells, the cell construct having a plurality of the biocompatible polymer blocks disposed in gaps between a plurality of the stem cells.

(2) The cartilage regenerative material according to (1), for use in regeneration of cartilage and bone.

(3) The cartilage regenerative material according to (1) or (2), in which the stem cells are mesenchymal stem cells.

(4) The cartilage regenerative material according to any one of (1) to (3), in which the cell construct includes the biocompatible polymer blocks in an amount of from 0.0000001 µg to 1µg per stem cell.

(5) The cartilage regenerative material according to any one of (1) to (4), in which the size of each of the biocompatible polymer blocks is from 10 µm to 300 µm.

(6) The cartilage regenerative material according to any one of (1) to (5), in which the thickness or the diameter of the cell construct is from 100 µm to 1 cm.

(7) The cartilage regenerative material according to any one of (1) to (6), in which the biocompatible polymer blocks are formed from a recombinant peptide or a chemically synthesized peptide.

(8) The cartilage regenerative material according to any one of (1) to (7), in which the biocompatible polymer blocks are formed from a recombinant gelatin or a chemically synthesized gelatin.

(9) The cartilage regenerative material according to (8), in which the recombinant gelatin or the chemically synthesized gelatin is represented by Formula 1,

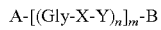

Formula 1:

in Formula 1, n units of X each independently represent any amino acid residue; n units of Y each independently represent any amino acid residue; m represents an integer from 2 to 10; n represents an integer from 3 to 100; A represents an arbitrary amino acid residue or amino acid sequence; and B represents an arbitrary amino acid residue or amino acid sequence.

(10) The cartilage regenerative material according to (8) or (9), in which the recombinant gelatin or the chemically synthesized gelatin is any one of the following:

a peptide comprising the amino acid sequence set forth in SEQ ID NO:1;

a peptide having biocompatibility and comprising an amino acid sequence obtained by modifying the amino acid sequence set forth in SEQ ID NO:1 by deletion, substitution or addition of one or several amino acid residues; and a peptide having biocompatibility and comprising an amino acid sequence having at least 80% sequence identity with the amino acid sequence set forth in SEQ ID NO:1.

(11) The cartilage regenerative material according to any one of (1) to (10), in which biocompatible polymers in the biocompatible polymer blocks are crosslinked by means of heat, ultraviolet radiation, or an enzyme.

(12) The cartilage regenerative material according to any one of (1) to (11), in which the biocompatible polymer blocks are in the form of granules obtainable by pulverizing a biocompatible polymer in the form of a porous body.

(13) A cartilage regenerative material comprising the cartilage regenerative material according to any one of (1) to (12) and a biocompatible polymer film.

(14) The cartilage regenerative material according to (13), in which the biocompatible polymer film is a film for isolating a portion or the entirety of the transplant face of the cell construct from the site of transplantation.

(15) A cell construct for use in cartilage regeneration therapy, the cell construct comprising biocompatible polymer blocks and stem cells, the cell construct having a plurality of the biocompatible polymer blocks disposed in gaps between a plurality of the stem cells.

(16) A method for regenerating cartilage, the method comprising a step of transplanting a cell construct that includes biocompatible polymer blocks and stem cells to a patient in need of cartilage regeneration, in which the cell construct has a plurality of the biocompatible polymer blocks disposed in gaps between a plurality of the stem cells.

(17) Use of a cell construct for the production of a cartilage regenerative material, the cell construct comprising biocompatible polymer blocks and stem cells, in which the cell construct has a plurality of the biocompatible polymer blocks disposed in gaps between a plurality of the stem cells.

The cartilage regenerative material of the invention has excellent cartilage regenerative capacity and excellent bone regenerative capacity, and is useful for cell transplantation therapy.

DESCRIPTION OF THE PREFERRED EMBODIMENTS

Figure 1:
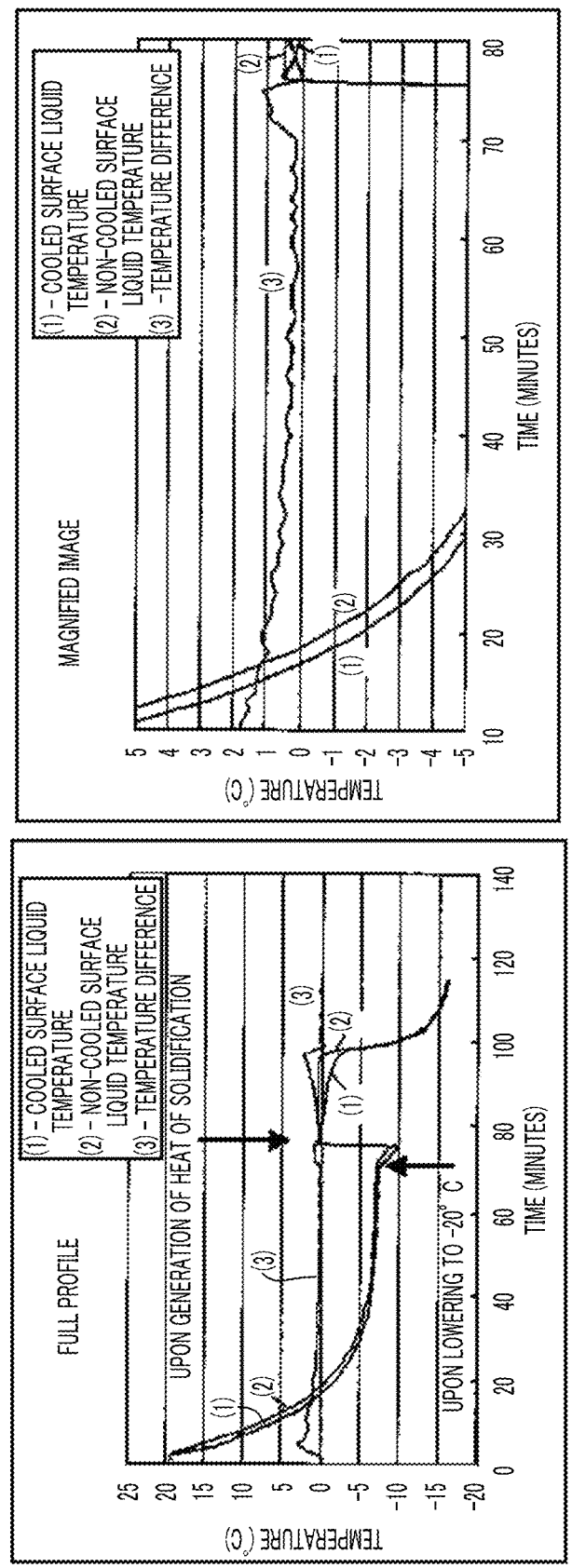
FIG. 1 illustrates a liquid temperature profile obtained under Condition A.

Hereinafter, embodiments of the invention will be explained in detail.

The cartilage regenerative material of the invention is a material comprising a cell construct that includes biocompatible polymer blocks and stem cells, the cell construct having a plurality of the biocompatible polymer blocks disposed in gaps between a plurality of the stem cells. The cell construct used in the invention may also be referred to as mosaic cell mass (cell mass in a mosaic state) in the present specification.

Since the cartilage regenerative material of the invention has excellent cartilage regenerative capacity and excellent bone regenerative capacity, in addition to the use for regenerating cartilage, the cartilage regenerative material can also be used in order to regenerate cartilage and bone. The cartilage regenerative material of the invention can be used as, for example, a transplant material to be transplanted into a cartilage defect site.

It is a completely unexpected, remarkable effect that a cell construct including biocompatible polymer blocks and stem cells, in which a plurality of the biocompatible polymer blocks are disposed in gaps between a plurality of the stem cells, has excellent cartilage regeneration action as well as excellent bone regeneration action. In JP4122280B and J. I. Lee, "Transplantation of scaffold-free spheroids composed of synovium-derived cells and chondrocytes or the treatment of cartilage defects of the knee," *European Cells and Materials*, Vol. 22, 2011, p 275-290, it is neither disclosed nor suggested to use biocompatible polymer blocks. The technologies disclosed in JP4122280B and J. I. Lee, "Transplantation of scaffold-free spheroids composed of synovium-derived cells and chondrocytes or the treatment of cartilage defects of the knee," *European Cells and Materials*, Vol. 22, 2011, p 275-290, are characterized in that a scaffold such as biocompatible polymer blocks is not included, and these technologies are different from the present invention from this point of view. It is described in WO2011/108517A that the cell construct produces a large amount of glycosaminoglycan (GAG); however, the amount of GAG production is irrelevant to the capability of simultaneously regenerating cartilage and bone. Chondrocyte differentiation and cartilage regeneration are different phenomena, and the cartilage regenerative capacity and the bone regenerative capacity are conceptually completely different. The GAG production in WO2011/108517A was achieved in an ex vivo experiment using a particular medium (chondrocyte differentiation medium) that promotes chondrocyte differentiation, and the conditions for this experiment are significantly different from the environment in vivo. Therefore, according to the findings of WO2011/108517A, cartilage regeneration in the in vivo environment cannot be expected, and particularly, it cannot be expected at all from WO2011/108517A that cartilage and bone can be regenerated simultaneously.

(1) Biocompatible polymer blocks

The cell construct used in the invention includes biocompatible polymer blocks. The biocompatible polymer blocks will be explained below.

(1-1) Biocompatible polymer

Biocompatibility means that in a case in which the material is brought into contact with a living body, the material does not give a rise to a noticeably harmful reaction such as a long-term and chronic inflammation reaction. Whether the biocompatible polymer used in the invention is decomposed in vivo is not particularly limited, as long as the polymer has biocompatibility; however, it is preferable that the polymer is a biodegradable polymer. Specific examples of a non-biodegradable polymer include polytetrafluoroethylene (PTFE), polyurethane, polypropylene, polyester, vinyl chloride, polycarbonate, acryl, stainless steel, titanium, silicone, and MPC (2-methacryloyloxyethylphosphorylcholine). Specific examples of a biodegradable polymer include polypeptides such as a recombinant peptide and a chemically synthesized peptide (for example, gelatin that will be explained below), polylactic acid, polyglycolic acid, a lactic acid-glycolic acid copolymer (PLGA), hyaluronic acid, glycosaminoglycan, proteoglycan, chondroitin, cellulose, agarose, carboxymethyl cellulose, chitin, and chitosan. Among the compounds described above, a recombinant peptide is particularly preferred. These biocompatible polymers may be devised in order to increase the cell adhesiveness. Specifically, methods such as "coating of a base material surface with a cell adhesion matrix (fibronectin, vitronectin, or laminin) or a cell adhesion sequence (an RGD sequence, a LDV sequence, a REDV (SEQ ID NO: 2) sequence, a YIGSR (SEQ ID NO: 3) sequence, a PDSGR (SEQ ID NO: 4) sequence, a RYVVLPR (SEQ ID NO: 5) sequence, a LGTIPG (SEQ ID NO: 6) sequence, a RNIAEIIKDI (SEQ ID NO: 7) sequence, an IKVAV (SEQ ID NO: 8) sequence, a LRE sequence, a DGEA (SEQ ID NO: 9) sequence, or a HAV sequence; all indicated by one-letter codes of amino acids) peptide", "amination or cationization of the base material surface", or "hydrophilic treatment of the base material surface by a plasma treatment or corona discharge" can be used.

The type of the polypeptide such as a recombinant peptide or a chemically synthesized peptide is not particularly limited as long as the polypeptide has biocompatibility; however, for example, gelatin, collagen, elastin, fibronectin, pronectin, laminin, tenascin, fibrin, fibroin, entactin, thrombospondin, and retronectin are preferred, while gelatin, collagen, and atelocollagen are most preferred. Gelatin that is intended to be used in the invention is preferably naturally occurring gelatin, a recombinant gelatin, or a chemically synthesized gelatin, and more preferred is a recombinant gelatin. The term naturally occurring gelatin as used herein means a gelatin produced from naturally occurring collagen.

The term chemically synthesized peptide or chemically synthesized gelatin means a peptide or gelatin that has been artificially synthesized. Synthesis of a peptide such as gelatin may be solid-phase synthesis or liquid-phase synthesis; however, solid-phase synthesis is preferred. Solid-phase synthesis of peptides is well known to those ordinarily skilled in the art, and examples include a Fmoc group synthesis method of using a Fmoc group (Fluorenyl-Methoxy-Carbonyl group) as a protective group for an amino group; and a Boc group synthesis method of using a Boc group (tert-ButylOxyCarbonyl group) as a protective group for an amino group. Regarding preferred embodiments of the chemically synthesized gelatin, the matters described in section (1-3) Recombinant gelatin given below in the present specification can be applied.

Recombinant gelatin will be explained below in the present specification.

The hydrophilicity value "1/IOB" value of the biocompatible polymer used in the invention is preferably from 0 to 1.0. The hydrophilicity value is more preferably from 0 to 0.6, and even more preferably from 0 to 0.4. IOB is an index of hydrophilicity/hydrophobicity based on an organic conceptual diagram showing the polarity/non-polarity of organic compounds suggested by FUJITA, Atsushi, and the details thereof are explained in, for example, "Pharmaceutical Bulletin", Vol. 2, 2, pp. 163-173 (1954), "Kagaku no Ryoiki (Domain of Chemistry)", Vol. 11, 10, pp. 719-725 (1957), and "Fragrance Journal", Vol. 50, pp. 79-82 (1981). To describe briefly, the root of all organic compounds is considered to be methane (CH4), and other compounds are all regarded as derivatives of methane. Certain values are set respectively for the number of carbon atoms, substituents, modified parts, rings, and the like of the compounds, and the scores are added to determine the organic values (OV) and the inorganic values (IV). These values are plotted on a graph, with the X-axis representing the organic values and the Y-axis representing the inorganic values. The IOB in the organic conceptual diagram means the ratio of the inorganic value (IV) with respect to the organic value (OV) in the organic conceptual diagram, that is, "inorganic value (IV)/organic value (OV)". Regarding the details of the organic conceptual diagram, reference can be made to "Shinpan Yuki Gainenzu-Kiso to Oyo-(New Edition Organic Conceptual Diagram—Fundamentals and Applications-)" (written by KODA, Yoshio, et al., Sankyo Shuppan Co., Ltd., 2008). In the present specification, hydrophilicity and hydrophobicity is indicated with the "1/IOB" value, which is the reciprocal of IOB. As the "1/IOB" value is smaller (closer to 0), this indicates that the compound is hydrophilic.

By adjusting the "1/IOB" value of the biocompatible polymer used in the invention to the range described above, the biocompatible polymer has higher hydrophilicity and has enhanced water absorbing properties. Accordingly, it is speculated that the high hydrophilicity acts effectively on the retention of nutrient components, and consequently contributes to the stabilization and ease of survival of cells in the cell construct (mosaic cell mass) according to the invention.

In a case in which the biocompatible polymer used in the invention is a polypeptide, the hydrophilicity/hydrophobicity index represented by the Grand average of hydropathicity (GRAVY) value of the polypeptide is preferably 0.3 or lower and −9.0 or higher, and more preferably 0.0 or lower and −7.0 or higher. The Grand average of hydropathicity (GRAVY) value can be obtained by the method described in "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appel R. D., Bairoch A.; ExPASy: the proteomics server for in-depth protein knowledge and analysis.; Nucleic Acids Res. 31: 3784-3788 (2003)".

By adjusting the GRAVY value of the biocompatible polymer used in the invention to the range described above, the biocompatible polymer has higher hydrophilicity and has enhanced water absorbing properties. Accordingly, it is speculated that the high hydrophilicity acts effectively on the retention of nutrient components, and consequently contributes to the stabilization and ease of survival of cells in the cell construct (mosaic cell mass) according to the invention.

(1-2) Crosslinking

The biocompatible polymer used in the invention may be a crosslinked polymer, or may be a polymer that is not crosslinked; however, a crosslinked polymer is preferred. By using a crosslinked biocompatible polymer, there is obtained an effect that in a case in which the cartilage regenerative material of the invention is cultured in a medium, and in a case which the cartilage regenerative material is transplanted into a living body, the cartilage regenerative material being instantaneously decomposed is prevented. Regarding general crosslinking methods, thermal crosslinking, crosslinking by means of an aldehyde (for example, formaldehyde or glutaraldehyde), crosslinking by means of a condensing agent (carbodiimide, cyanamide, or the like), enzymatic crosslinking, photocrosslinking, ultraviolet crosslinking, hydrophobic interaction, hydrogen bonding, ionic interaction, and the like are known. The crosslinking method used in the invention is preferably thermal crosslinking, ultraviolet crosslinking, or enzymatic crosslinking, and particularly preferably thermal crosslinking.

In a case in which enzyme-induced crosslinking is carried out, the enzyme is not particularly limited as long as the enzyme has an effect of crosslinking between polymer molecules; however, preferably a transglutaminase and a laccase, and most preferably a transglutaminase, can be used. There are no particular limitations on specific examples of the polymer that is enzymatically crosslinked by a transglutaminase as long as the polymer is a protein having a lysine residue and a glutamine residue. The transglutaminase may be a mammal-derived enzyme or a microbially derived enzyme, and specifically, ACTIVA series manufactured by Ajinomoto Co., Inc., and mammal-derived transglutaminases that are released as reagents, for example, Guinea pig liver-derived transglutaminase, goat-derived transglutaminase, and rabbit-derived transglutaminase, which are products of Oriental Yeast Co., Ltd.; Upstate USA, Inc.; Biodesign International, Inc.; and the like, and human-derived blood coagulation factor (Factor XIIIa, Haematologic Technologies, Inc.).

The reaction temperature in the case of performing crosslinking (for example, thermal crosslinking) is not particularly limited as long as crosslinking is enabled; however, the reaction temperature is preferably −100° C. to 500° C., more preferably 0° C. to 300° C., even more preferably 50° C. to 300° C., still more preferably 100° C. to 250° C., and even more preferably 120° C. to 200° C.

(1-3) Recombinant Gelatin

The recombinant gelatin as used herein means a polypeptide or protein-like substance having an amino acid sequence similar to that of gelatin, which is produced by a gene recombination technology. It is preferable that the recombinant gelatin that can be used in the invention has repeats of a sequence represented by Gly-X-Y (where X and Y each independently represent any amino acid residue), which is characteristic to collagen. Here, a plurality of the Gly-X-Y sequences may be identical to or different from one another.

Preferably, two or more sequences of cell adhesion signals are included in one molecule. Regarding the recombinant gelatin that is used in the invention, a recombinant gelatin having an amino acid sequence derived from a partial amino acid sequence of collagen can be used. For example, the recombinant gelatins described in EP1014176B, U.S. Pat. No. 6,992,172B, WO2004/85473A, and WO2008/103041A can be used; however, the examples are not limited to these. Preferred examples of the recombinant gelatin that is used in the invention are recombinant gelatins of the following embodiments.

A recombinant gelatin has the original properties of naturally occurring gelatin and thus has excellent biocompatibility. Also, since it is not a substance derived from a natural source, a recombinant gelatin has no risk of bovine spongiform encephalopathy (BSE) or the like, and has an excellent characteristic of being non-infectious. Since a recombinant gelatin is homogeneous compared to naturally occurring gelatin and has a predetermined sequence, it is possible to precisely design a recombinant gelatin with fewer fluctuations, in connection with strength and degradability, through crosslinking or the like.

The molecular weight of the recombinant gelatin is not particularly limited; however, the molecular weight is preferably from 2,000 to 100,000 (from 2 kDa to 100 kDa), more preferably from 2,500 to 95,000 (from 2.5 kDa to 95 kDa), even more preferably from 5,000 to 90,000 (from 5 kDa to 90 kDa), and most preferably from 10,000 to 90,000 (from 10 kDa to 90 kDa).

It is preferable that the recombinant gelatin has repeats of a sequence represented by Gly-X-Y, which is characteristic to collagen. Here, a plurality of the Gly-X-Y sequences may be identical to or different from one another. In regard to the sequence Gly-X-Y, Gly represents glycine, and X and Y each represent an arbitrary amino acid (preferably, an arbitrary amino acid other than glycine). The sequence represented by Gly-X-Y characteristic to collagen is a highly specific partial structure present in the amino acid compositions and sequences of gelatin and collagen, compared to other proteins. In this partial structure, glycine accounts for about one-third of the whole composition, and in the amino acid sequence, glycine repeatedly appears at a rate of one in every three amino acid residues. Glycine is the simplest amino acid, and there are fewer restrictions to the arrangement in a molecular chain. Thus, glycine greatly contributes to regeneration of the helix structure in the case of gelation. It is preferable that the amino acids represented by X and Y include a large proportion of imino acids (proline and oxyproline), and imino acids account for 10% to 45% of the total amount of the amino acids. Preferably, amino acids that account for 80% or more, more preferably 95% or more, and most preferably 99% or more, of the sequence of the recombinant gelatin, constitute the repeating structure of Gly-X-Y.

In general gelatins, polar amino acids that have an electric charge and polar amino acids that are uncharged exist at a ratio of 1:1. Here, the term polar amino acid specifically refers to cysteine, aspartic acid, glutamic acid, histidine, lysine, asparagine, glutamine, serine, threonine, tyrosine, or arginine, and among these, polar uncharged amino acids include cysteine, asparagine, glutamine, serine, threonine, and tyrosine. In regard to the recombinant gelatin used in the invention, the proportion of polar amino acids among all the amino acids that constitute the recombinant gelatin is 10% to 40%, and preferably 20% to 30%. Meanwhile, the proportion of uncharged amino acids in the polar amino acids is preferably 5% or more and less than 20%, and more preferably 5% or more and less than 10%. It is also preferable that any one amino acid, and preferably 2 or more amino acids, of serine, threonine, asparagine, tyrosine, and cysteine are not included in the amino acid sequence.

Generally, in regard to polypeptides, minimal amino acid sequences that function as cell adhesion signal sequences are known (for example, "Byotai Seiri (Pathophysiology)", Vol. 9, No. 7 (1990), p. 527, published by Nagai Shoten Co., Ltd.). It is preferable that the recombinant gelatin used in the invention contains two or more such minimal amino acid sequences that function as cell adhesion signals in one molecule. Regarding specific sequences, from the viewpoint of being applicable to many kinds of adhering cells, an RGD sequence, a LDV sequence, a REDV (SEQ ID NO: 2) sequence, a YIGSR (SEQ ID NO: 3) sequence, a PDSGR (SEQ ID NO: 4) sequence, a RYVVLPR (SEQ ID NO: 5) sequence, a LGTIPG (SEQ ID NO: 6) sequence, a RNIAEIIKDI (SEQ ID NO: 7) sequence, an IKVAV (SEQ ID NO: 8) sequence, a LRE sequence, a DGEA (SEQ ID NO: 9) sequence, and a HAV sequence, which are expressed in one-letter codes of amino acids, are preferred. More preferred sequences include an RGD sequence, a YIGSR (SEQ ID NO: 3) sequence, a PDSGR (SEQ ID NO: 4) sequence, a LGTIPG (SEQ ID NO: 6) sequence, an IKVAV (SEQ ID NO: 8) sequence, and a HAV sequence, and particularly preferred is an RGD sequence. Among RGD sequences, an ERGD (SEQ ID NO: 10) sequence is preferred. When a recombinant gelatin having cell adhesion signal sequences is used, the amount of cell matrix production can be increased. For example, in a case in which mesenchymal stem cells are used as cells, the production of glycosaminoglycans (GAG) in chondrocyte differentiation can be increased.

In regard to the disposition of RGD sequences in the recombinant gelatin used in the invention, it is preferable that the number of amino acids between RGD sequences is between 0 and 100, and preferably between 25 and 60, and is not uniform.

The content of these minimal amino acid sequences is preferably 3 to 50, more preferably 4 to 30, even more preferably 5 to 20, and most preferably 12, in one molecule of protein, from the viewpoints of cell adhesion and proliferation properties.

In regard to the recombinant gelatin used in the invention, the proportion of the RGD sequences (motifs) with respect to the total number of amino acid residues is preferably at least 0.4%. In a case in which a recombinant gelatin includes 350 or more amino acid residues, it is preferable that each stretch of 350 amino acid residues includes at least one RGD motif. The proportion of the RGD motif with respect to the total number of amino acid residues is more preferably at least 0.6%, even more preferably at least 0.8%, still more preferably at least 1.0%, even more preferably at least 1.2%, and most preferably at least 1.5%. The number of RGD motifs within a recombinant peptide is preferably at least 4, more preferably at least 6, even more preferably at least 8, still more preferably from 12 to 16, per 250 amino acid residues. The proportion of 0.4% of the RGD motifs corresponds to at least one RGD sequence per 250 amino acid residues. Since the number of the RGD motifs is an integer, in order to satisfy the characteristic requirement of 0.4%, a gelatin molecule containing 251 amino acid residues must include at least two RGD sequences. Preferably, the recombinant gelatin of the invention includes at least two RGD sequences per 250 amino acid residues; more preferably includes at least three RGD sequences per 250 amino acid residues; and even more preferably includes at least four RGD sequences per 250 amino acid residues. According to another embodiment of the recombinant gelatin of the invention, the recombinant gelatin includes at least four RGD motifs, preferably at least six RGD motifs, more preferably at least eight RGD motifs, and still more preferably from 12 to 16 RGD motifs.

The recombinant gelatin may be partially hydrolyzed.

Preferably, the recombinant gelatin used in the invention is represented by Formula 1: A-[(Gly-X-Y)$_n$]$_m$-B. n units of X each independently represent any one amino acid residue, and n units of Y each independently represent any one amino acid residue. m represents an integer from 2 to 10, and preferably 3 to 5. n represents an integer from 3 to 100, preferably 15 to 70, and more preferably 50 to 65. A represents an arbitrary amino acid residue or amino acid sequence, and B represents an arbitrary amino acid residue or amino acid sequence.

More preferably, the recombinant gelatin used in the invention is represented by formula (SEQ ID NO: 11): Gly-Ala-Pro-[(Gly-X-Y)$_{63}$]$_3$-Gly (in the formula, 63 units of X each independently represent any one amino acid residue; 63 units of Y each independently represent any one amino acid residue; and 63 units of Gly-X-Y may be identical to or different from one another).

It is preferable that a plurality of the sequence units of naturally occurring collagen are bonded to the repeating unit. The naturally occurring collagen as used herein may be any collagen substance that exists in nature; however, the collagen is preferably type I, type II, type III, type IV, or type V collagen. The collagen is more preferably type I, type II, or type III collagen. According to another embodiment, the source of the above-mentioned collagens is preferably human, cow, pig, mouse, or rat, and more preferably a human source.

The isoelectric point of the recombinant gelatin used in the invention is preferably 5 to 10, more preferably 6 to 10, and even more preferably 7 to 9.5.

Preferably, the recombinant gelatin is not deaminated.

Preferably, the recombinant gelatin does not have a telopeptide.

Preferably, the recombinant gelatin is a substantially pure polypeptide produced from a nucleic acid that encodes an amino acid sequence.

The recombinant gelatin used in the invention is particularly preferably:

(1) a peptide comprising the amino acid sequence set forth in SEQ ID NO:1;

(2) a peptide having biocompatibility and comprising an amino acid sequence obtained by modifying the amino acid sequence set forth in SEQ ID NO:1 by deletion, substitution or addition of one or several amino acid residues; or (3) a peptide having biocompatibility and comprising an amino acid sequence having at least 80% (preferably at least 90%, more preferably at least 95%, and most preferably at least 98%) sequence identity with the amino acid sequence set forth in SEQ ID NO:1.

The term "one or several" in the phrase "amino acid sequence obtained by modifying ... by deletion, substitution or addition of one or several amino acid residues" means preferably 1 to 20, more preferably 1 to 10, even more preferably 1 to 5, and particularly preferably 1 to 3.

The recombinant gelatin used in the invention can be produced by a gene recombination technology that is known to those ordinarily skilled in the art, and the recombinant gelatin can be produced according to the methods described in, for example, EP1014176A2, U.S. Pat. No. 6,992,172B, WO2004/85473A, and WO2008/103041A. Specifically, a gene that encodes the amino acid sequence of a predetermined recombinant gelatin is obtained, this is incorporated into an expression vector to produce a recombinant expression vector, and this is introduced into an appropriate host. Thus, a transformant is produced. The transformant thus obtained is cultured in an appropriate medium, and thereby, a recombinant gelatin is produced. Then, the recombinant gelatin thus produced is collected from the culture product. Thereby, the recombinant gelatin used in the invention can be produced.

(1-4) Biocompatible Polymer Blocks

According to the invention, blocks (masses) comprising the above-described biocompatible polymer are used.

The shape of the biocompatible polymer blocks according to the invention is not particularly limited. For example, the shape is an irregular shape, a spherical form, a particulate (granular) form, a powder form, a porous form (porous body), a fibrous form, a spindle shape, a flat shape, and a sheet form, and preferred examples of the shape include an irregular shape, a spherical form, a particulate (granular) form, a powder form, and a porous form. An irregular shape implies that the surface shape is not uniform, and for example, it is implied that the shape has concavities and convexities such as a rock. Examples of the shape mentioned above are not separate and isolated, and for example, the polymer block may have an irregular shape as an example of a subordinate concept of the particulate (granular) form.

The size of one biocompatible polymer block according to the invention is not particularly limited; however, the size is preferably from 1 μm to 1,000 μm, more preferably from 10 μm to 1,000 μm, even more preferably from 10 μm to 700 μm, still more preferably from 10 μm to 300 μm, even more preferably from 10 μm to 200 μm, still more preferably from 20 μm to 200 μm, particularly preferably from 20 μm to 150 μm, and most preferably from 50 μm to 110 μm. It is preferable from the viewpoint of cartilage regeneration that the size of one biocompatible polymer block is adjusted to be in the range described above. The size of one biocompatible polymer block is not intended to mean that the average value of the size of a plurality of the biocompatible polymer blocks is in the range described above, but is intended to mean the size of each of individual biocompatible polymer blocks obtainable by sieving a plurality of the biocompatible polymer blocks.

The size of one block can be defined by the size of the sieve used in the case of classifying the blocks. For example, in a case in which blocks that have passed through a sieve having a mesh size of 180 μm are sieved through a sieve having a mesh size of 106 μm, the blocks remaining on the sieve can be defined as blocks having a size of 106 to 180 μm. Next, in a case in which the blocks that have passed through the sieve having a mesh size of 106 μm are sieved through a sieve having a mesh size of 53 μm, the blocks remaining on the sieve can be defined as blocks having a size of 53 to 106 μm. Next, in a case in which the blocks that have passed through the sieve having a mesh size of 53 μm are sieved through a sieve having a mesh size of 25 μm, the blocks remaining on the sieve can be defined as blocks having a size of 25 to 53 μm.

(1-5) Method for Producing Biocompatible Polymer Blocks

The method for producing biocompatible polymer blocks is not particularly limited; however, for example, irregularly shaped biocompatible polymer blocks, which constitute an example of a granular form, can be obtained by pulverizing a porous body of a biocompatible polymer using a pulverizing machine (NEW POWER MILL or the like).

The method for producing a porous body of a biocompatible polymer is not particularly limited; however, for example, there may be mentioned a production method including:

(a) a step of cooling a solution of a biocompatible polymer to an unfrozen state at a temperature at which the difference between the temperature of a part having the highest liquid temperature in the solution and the temperature of a part having the lowest liquid temperature in the solution is 2.5° C. or less, and the temperature of the part having the highest liquid temperature in the solution is lower than or equal to the melting point of the solvent;

(b) a step of freezing the solution in an unfrozen state of the biocompatible polymer obtained in Step (a); and (c) a step of freeze-drying the frozen solution of the biocompatible polymer obtained in Step (b).

In a case in which the biocompatible polymer solution is cooled to an unfrozen state, as the difference between the temperature of a part having the highest liquid temperature in the solution and the temperature of a part having the lowest liquid temperature in the solution is adjusted to be 2.5° C. or less (preferably 2.3° C. or less, and more preferably 2.1° C. or less), that is, as the difference in temperature is adjusted to be smaller, the difference in the size of the pores in the porous body thus obtainable is made smaller. The lower limit of the difference between the temperature of a part having the highest liquid temperature in the solution and the temperature of a part having the lowest liquid temperature in the solution is not particularly limited, and the temperature difference may be 0° C. or more, and for example, may be 0.1° C. or more, 0.5° C. or more, 0.8° C. or more, or 0.9° C. or more. Thereby, an effect that the cell construct obtained by using the biocompatible polymer blocks produced using a porous body of the biocompatible polymer thus produced presents a high cell population, is achieved.

In regard to the cooling of Step (a), it is preferable to perform cooling by means of, for example, a material having a thermal conductivity lower than that of water (preferably, TEFLON (registered trademark)), and the part having the highest liquid temperature in the solution can be assumed to be a part remotest from the cooling surface, and the part having the lowest liquid temperature in the solution can be assumed to be the liquid temperature at the cooling surface.

Preferably, in Step (a), the difference between the temperature of a part having the highest liquid temperature in the solution and the temperature of a part having the lowest liquid temperature in the solution immediately before the generation of the heat of solidification is 2.5° C. or less, more preferably 2.3° C. or less, and even more preferably 2.1° C. or less. Here, the "temperature difference immediately before the generation of the heat of solidification" means the temperature difference at the time when the temperature difference becomes the largest in a time period between 1 second and 10 seconds before the generation of the heat of solidification.

Preferably, in Step (a), the temperature of a part having the lowest liquid temperature in the solution is (melting point of the solvent −5° C.) or lower, more preferably (melting point of the solvent −5° C.) or lower and (melting point of the solvent −20° C.) or higher, and even more preferably (melting point of the solvent −6° C.) or lower and (melting point of the solvent −16° C.) or higher. The solvent of the "melting point of the solvent" is the solvent of the solution of the biocompatible polymer.

In Step (b), the solution of the biocompatible polymer in an unfrozen state obtained in Step (a) is frozen. The cooling temperature for freezing in Step (b) is not particularly limited and may vary depending on the cooling equipment. Preferably, the cooling temperature is a temperature lower by 3° C. to 30° C., more preferably a temperature lower by 5° C. to 25° C., and even more preferably a temperature lower by 10° C. to 20° C., than the temperature of the part having the lowest liquid temperature in the solution.

In Step (c), the frozen solution of the biocompatible polymer obtained in Step (b) is freeze-dried. Freeze-drying can be carried out by a conventional method, and for example, freeze-drying can be carried out by performing vacuum drying at a temperature lower than the melting point of the solvent, and further performing vacuum drying at room temperature (20° C.).

(2) Stem Cells

Regarding the stem cells to be used in the invention, any arbitrary stem cells can be used as long as the stem cells are capable of cell transplantation and are capable of exhibiting cartilage regenerative capacity, and the type of the cells is not particularly limited. One type of stem cells may be used, or a combination of multiple types of stem cells may also be used. The stem cells to be used are preferably animal cells, more preferably vertebrate-derived cells, and particularly preferably human-derived cells. The type of the vertebrate-derived cells (particularly, human-derived cells) may be any of pluripotent cells and somatic stem cells. Regarding the pluripotent cells, for example, embryonic stem cells (ES cells), germline stem cells (GS cells), or induced pluripotent stem cells (iPS cells) can be used. Regarding the somatic stem cells, for example, mesenchymal stem cells (MSC), amniotic cells, cord blood- derived cells, bone marrow-derived cells, or adipose-derived stem cells can be used, and particularly preferred are mesenchymal stem cells (MSC). The origin of the cells may be any of autologous cells and heterologous cells.

(3) Cell Construct

According to the invention, a cell construct is produced using the biocompatible polymer blocks and the stem cells described above, by disposing a plurality of the biocompatible polymer blocks in gaps between a plurality of the stem cells three-dimensionally in a mosaic pattern. As the biocompatible polymer blocks and the stem cells are disposed three-dimensionally in a mosaic pattern, a cell construct in which the stem cells are uniformly distributed in the cell construct is formed, and delivery of nutrients such as medium components from the outside to the interior of the cell construct is enabled.

In the cell construct used in the invention, a plurality of biocompatible polymer blocks are disposed in gaps between a plurality of stem cells, and here, the "gaps between stem cells" need not be spaces closed by the constituting stem cells, and may be spaces sandwiched between the stem cells. Furthermore, it is not necessary that gaps should be provided everywhere in between the stem cells, and there may be sites where the stem cells are in contact. The distance of a gap between stem cells that sandwich the biocompatible polymer blocks therebetween, that is, the distance of the gap in the case of selecting a certain stem cell and another stem cell that exists in the shortest distance from the foregoing stem cell, is not particularly limited. However, it is preferable that the distance is equal to the size of the biocompatible polymer block, and a suitable distance is also in the range of a suitable size of the biocompatible polymer block.

The biocompatible polymer blocks are configured to be interposed between stem cells; however, it is not necessary that stem cells should be present between all the biocompatible polymer blocks, and there may be sites where the biocompatible polymer blocks are in contact. The distance between the biocompatible polymer blocks sandwiching stem cells therebetween, that is, the distance in the case of selecting a biocompatible polymer block and another biocompatible polymer block that exists in the shortest distance from the foregoing biocompatible polymer block, is not particularly limited. However, the distance is preferably the size of a mass of the stem cells obtainable in the case of gathering one to several stem cells that are used, and for example, the distance is from 10 μm to 1,000 μm, preferably from 10 μm to 100 μm, and even more preferably from 10 μm to 50 μm.

In the present specification, the expression "uniformly distributed" is used in the phrase "cell construct in which stem cells are uniformly distributed in the cell construct" and the like; however, this does not mean perfect uniformity, and it is meant that delivery of nutrients such as medium components from the outside to the interior of the cell construct is enabled.

The thickness or diameter of the cell construct can be adjusted to any desired thickness; however, as the lower limit, the thickness is preferably 215 μm or more, more preferably 400 μm or more, and even more preferably 500 μm or more. The upper limit of the thickness or diameter is not particularly limited; however, as a general range for practical use, the upper limit is preferably 3 cm or less, more preferably 2 cm or less, and even more preferably 1 cm or less. The range of the thickness or diameter of the cell construct is preferably from 400 μm to 3 cm, more preferably from 500 μm to 2 cm, and even more preferably from 500 μm to 1 cm. By having the thickness or diameter of the cell construct adjusted to be in the range described above, the cell construct can easily manifest the cartilage regenerative capacity.

In the cell construct, preferably, regions comprising biocompatible polymer blocks and regions comprising stem cells are arranged in a mosaic pattern. The "thickness or diameter of the cell construct" according to the present specification is intended to represent the following. In a case in which a certain point A inside the cell construct is selected, among straight lines that pass through the point A, a line segment that divides the cell construct such that the distance from the outside the cell construct becomes the shortest, is selected, and the length of this line segment is designated as line segment A. A point A at which the line segment A becomes the longest inside the cell construct is selected, and the length of the line segment A in this case is designated as the "thickness or diameter of the cell construct".

The ratio of the stem cells and the biocompatible polymer blocks in the cell construct is not particularly limited; however, the mass of the biocompatible polymer block per stem cell is preferably from 0.0000001 μg to 1 μg, more preferably from 0.000001 μg to 0.1 μg, even more preferably from 0.00001 μg to 0.01 μg, and most preferably from 0.00002 μg to 0.006 μg. As the ratio between the stem cells and the biocompatible polymer blocks is adjusted to the range described above, the stem cells can be distributed more uniformly. By adjusting the lower limit to the range described above, the effects of the stem cells can be manifested in a case in which the cell construct is used for the above-described applications, and by adjusting the upper limit to the range described above, any components that optionally exist in the biocompatible polymer blocks can be supplied to the stem cells. Here, the components in the biocompatible polymer blocks are not particularly limited, and the components may be the components included in the medium that will be described below.

(4) Method for Producing Cell Construct

A cell construct can be produced by mixing biocompatible polymer blocks and stem cells. More specifically, a cell construct can be produced by alternately disposing the biocompatible polymer blocks and the stem cells. The production method is not particularly limited; however, a method of forming the biocompatible polymer blocks and then inoculating the stem cells is preferred.

Specifically, a cell construct can be produced by incubating a mixture of biocompatible polymer blocks and a stem cell-containing culture fluid. For example, in a container, stem cells and biocompatible polymer blocks that have been produced in advance are disposed in a mosaic pattern in a liquid that is retained in the container. Regarding the means for disposition, it is preferable to promote or control the formation of the mosaic-patterned arrangement formed from stem cells and biocompatible polymer blocks by using spontaneous aggregation, gravity drop, centrifugation, or stirring.

Regarding the container used, a container formed from a low-cell-adhesive material or a non-cell-adhesive material is preferred, and a container formed from polystyrene, polypropylene, polyethylene, glass, polycarbonate, or polyethylene terephthalate is more preferred. The shape of the bottom face of the container is preferably a flat bottom type, a U-shaped form, or a V-shaped form.

In regard to the cell construct having a mosaic-patterned arrangement that is obtained by the method described above, a cell construct having a desired size can be produced by, for example, a method such as:

(a) integrating mosaic-patterned cell masses that have been produced separately, or (b) increasing the volume in a differentiation medium or a proliferation medium. The method of integration and the method of increasing the volume are not particularly limited.

For example, during the process of incubating a mixture of biocompatible polymer blocks and a stem cell-containing culture fluid, the volume of the cell construct can be increased by replacing the medium with a differentiation medium or a proliferation medium. Preferably, during the process of incubating a mixture of biocompatible polymer blocks and a stem cell- containing culture fluid, a cell construct having a desired size, in which stem cells are uniformly distributed in the cell construct, can be produced by further adding biocompatible polymer blocks.

The method of integrating mosaic-patterned cell masses that have been produced separately is specifically a method for producing a cell construct, the method including a step of integrating a plurality of cell constructs, each of the cell constructs including a plurality of biocompatible polymer blocks and a plurality of stem cells, in which one or a plurality of the biocompatible polymer blocks are disposed in some or all of a plurality of gaps formed by a plurality of the stem cells.

It is preferable that the thickness or diameter of each cell construct before integration or volume increase is from 10 µm to 1 cm, and the thickness or diameter after integration or volume increase is from 100 µm to 3 cm. Here, the thickness or diameter of each cell construct before integration is more preferably from 10 µm to 2,000 µm, even more preferably from 15 µm to 1,500 µm, and most preferably from 20 µm to 1,300 µm. The range of the thickness or diameter after integration is more preferably from 100 µm to 2 cm, even more preferably from 100 µm to 1 cm, still more preferably from 200 µm to 1 cm, and particularly preferably from 400 µm to 1 cm.

It is preferable that the cell constructs that need to be integrated are disposed at a distance of from 0 µm to 50 µm, and the distance is more preferably from 0 µm to 20 µm, and even more preferably from 0 µm to 5 µm. In a case in which the cell constructs are integrated, it is considered that as a result of proliferation and extension of the cells, the cells or the matrix produced by the cells accomplishes the role as an adhesive, and the cell constructs join together. Thus, adhesion between cell constructs is facilitated by adjusting the distance to the range described above.

A cell construct having a desired size can also be produced by further adding biocompatible polymer blocks. Specifically, second biocompatible polymer blocks can be further added to a cell construct including a plurality of first biocompatible polymer blocks and a plurality of stem cells, the cell construct having one or a plurality of the biocompatible polymer blocks disposed in some or all of a plurality of gaps formed by a plurality of the stem cells, and the mixture can be incubated.

It is preferable that the rate at which the second biocompatible polymer blocks are added in a case in which the second biocompatible polymer blocks are further added to the cell construct and incubated together, is appropriately selected in accordance with the rate of proliferation of the stem cells that are used.

Specifically, if the rate at which the second biocompatible polymer blocks are added is fast, the stem cells move to the outside of the cell construct, and the uniformity of the stem cells is decreased. If the rate of addition is slow, there occur sites where the proportion of the stem cells increases, and the uniformity of the stem cells is decreased. Therefore, the rate of addition is selected in consideration of the rate of proliferation of the stem cells used.

(5) Method of using Cartilage Regenerative Material

According to the invention, the cell construct described above is used as a cartilage regenerative material. The cartilage regenerative material of the invention can be used for the purpose of cell transplantation to a diseased site of cartilage defect. Examples of the disease associated with cartilage defect include, but are not particularly limited to, arthrosis deformans, osteochondral defect, osteochondritis dissecans, traumatic cartilage injury, osteoarthritis, relapsing polychondritis, achondroplasia, injury of intervertebral discs, and hernia of intervertebral discs.

Examples of the transplantation method include methods using incision, injection, an arthroscope, and an endoscope. Regarding the cell construct of the invention, unlike cell transplants such as a cell sheet, the size of the construct can be made small, and therefore, a less invasive transplantation method such as transplantation by injection is enabled.

The amount used in the case of transplanting the cartilage regenerative material of the invention can be appropriately selected in accordance with the disease state or the like; however, the number of cells to be transplanted is preferably $1.0 \times 10^5$ cells/cm$^3$ to $1.0 \times 10^{10}$ cells/cm$^3$, and more preferably $1.0 \times 10^6$ cells/cm$^3$ to $1.0 \times 10^9$ cells/cm$^3$.

Regarding the number of times of transplantation of the cartilage regenerative material of the invention, transplantation may be performed only once, or transplantation may be performed two or more times as necessary.

(6) Biocompatible Polymer Film

The cartilage regenerative material of the invention as described above may be used alone as a cartilage regenerative material; however, the cartilage regenerative material can also be used in combination with a biocompatible polymer film as a cartilage regenerative material. The cartilage regenerative material of the invention and the biocompatible polymer film described above may be supplied separately in the form of kits, or the cartilage regenerative material of the invention and the biocompatible polymer film may also be supplied in the form of a product bonded together. In a case in which the cartilage regenerative material and the biocompatible polymer film are supplied in the form of separate kits, the user can bond the cartilage regenerative material and the biocompatible polymer film together and then transplant the resultant. Alternatively, the user may transplant the biocompatible polymer film and then transplant the cartilage regenerative material.

In a case in which a biocompatible polymer film is used, it is preferable that the biocompatible polymer film is used as a film for isolating a portion or the entirety of the transplant face of the cell construct from the site of transplantation. For example, it is preferable that the biocompatible polymer film is transplanted first to the site of transplantation, and subsequently, the cell construct is transplanted on the top surface of the biocompatible polymer film (the surface on the opposite side of the surface that is in contact with the site of transplantation). Alternatively, in a case in which a cartilage regenerative material including the cell construct of the invention is bonded together with the biocompatible polymer film and then the resultant is transplanted, it is preferable that the biocompatible polymer film is transplanted so as to be brought into direct contact with the site of transplantation.

Specific examples and preferred ranges of the biocompatible polymer that constitutes the biocompatible polymer film are the same as those in the case of the biocompatible polymer that constitutes the biocompatible polymer blocks, and specifically, the specific examples and the preferred ranges are as described above in sections (1-1) Biocompatible polymer, (1-2) Crosslinking, and (1-3) Recombinant gelatin in the present specification. The biocompatible polymer that constitutes the biocompatible polymer film may be the same as, or may be different from, the biocompatible polymer that constitutes the biocompatible polymer blocks.

The method for producing a biocompatible polymer film is not particularly limited, and the production can be carried out by a conventional method. For example, a biocompatible polymer film can be produced by causing an aqueous solution of a biocompatible polymer to flow into a plastic tray, and drying the aqueous solution at low temperature (for example, in a refrigerator).

The biocompatible polymer film can be crosslinked. In a case in which the polymer film is crosslinked, the degree of crosslinking is not particularly limited; however, the degree of crosslinking is generally 4 to 15, and more preferably 6 to 13. The degree of crosslinking is the number of crosslinks per molecule. Measurement of the degree of crosslinking can be carried out using the TNBS (2,4,6-trinitrobenzenesulfonic acid) method described in section [7] Method for measuring degree of crosslinking in the Examples.

The rate of decomposition of the biocompatible polymer film varies depending on the degree of crosslinking. The rate of decomposition of the biocompatible polymer film can be measured and evaluated by the method described below in section [8] Method for measuring rate of decomposition in the Examples. The rate of decomposition of the biocompatible polymer film measured by the method is not particularly limited; however, the rate of decomposition is generally 0.1 to 10 [mass %/hour], and more preferably 0.5 to 6.9 [mass %/hour].

(7) Use and Cartilage Regeneration Method

According to the invention, there is provided a cell construct for use in the treatment of cartilage regeneration, the cell construct including biocompatible polymer blocks and stem cells, in which a plurality of the polymer blocks are disposed in gaps between a plurality of the stem cells. In addition to the cell construct, the biocompatible polymer film can also be used in combination. Preferred ranges of the biocompatible polymer blocks, the stem cells, the cell construct, and the biocompatible polymer film are the same as described above in the present specification.

According to the invention, there is provided a cartilage regeneration method including a step of transplanting the above-described cell construct to a patient in need of cartilage regeneration. In the cartilage regeneration method of the invention, the cell construct described above is used as a cartilage regenerative material. In the case of transplanting the cell construct, the biocompatible polymer film may be transplanted. Preferred ranges of the biocompatible polymer blocks, the stem cells, the cell construct, and the biocompatible polymer film are the same as described above in the present specification.

Furthermore, according to the invention, use of the cell construct for the production of a cartilage regenerative material is provided. In addition to the cell construct, the biocompatible polymer film can also be used in combination. Preferred ranges of the biocompatible polymer blocks, the stem cells, the cell construct, and the biocompatible polymer film are the same as described above in the present specification.

The invention will be explained more specifically by way of the following Examples; however, the invention is not intended to be limited by the following Examples.

EXAMPLES

[1] Recombinant Peptide (Recombinant Gelatin)

As a recombinant peptide (recombinant gelatin), the following CBE3 was prepared (described in WO2008/103041A).

CBE3:
Molecular weight: 51.6 kD
Structure: GAP[GXY]$_{63}$]$_3$G (SEQ ID NO: 11)
Number of amino acid residues: 571
RGD sequence: 12 sequences
Imino acid content: 33%

Almost 100% of the amino acid residues constitute a repeating structure of GXY. Serine, threonine, asparagine, tyrosine, and cysteine were not included in the amino acid sequence of CBE3. CBE3 comprises an ERGD (SEQ ID NO: 10) sequence.

Isoelectric point: 9.34
GRAVY value: −0.682
1/IOB value: 0.323

Amino acid sequence (SEQ ID NO:1 in the Sequence Listing) (Identical to SEQ ID NO:3 disclosed in WO2008/103041A. However, X at the end was corrected to "P")

GAP (GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP) 3G

Furthermore, a porous body and a sponge according to the present specification are synonyms.

[2] Production of Recombinant Peptide Porous Body

[PTFE Thick Cylindrical Container]

A cylindrical cup-shaped container made of polytetrafluoroethylene (PTFE) and having a bottom face thickness of 3 mm, a diameter of 51 mm, a lateral face thickness of 8 mm, and a height of 25 mm was prepared. The cylindrical cup was such that when the curved face was erected as the lateral face, the lateral face was closed with a PTFE plate having a thickness of 8 mm, and the bottom face (circular-shaped flat plate) was also closed with a PTFE plate having a thickness of 3 mm. Meanwhile, the cylindrical cup had an open top face. Therefore, the inner diameter of the cylindrical cup was 43 mm. Hereinafter, this container will be referred to as PTFE thick cylindrical container.

[Aluminum Glass Plate Cylindrical Container]

A cylindrical cup-shaped container made of aluminum and having a thickness of 1 mm and a diameter of 47 mm was prepared. The cylindrical cup was such that when the curved face was erected as the lateral face, the lateral face was closed with an aluminum plate with a thickness of 1 mm, and the bottom face (circular-shaped flat plate) was also closed with an aluminum plate having a thickness of 1 mm. Meanwhile, the cylindrical cup had an open top face. A TEFLON (registered trademark) plate having a thickness of 1 mm was uniformly lined over the entire surface on the inner side of the lateral face, and as a result, the inner diameter of the cylindrical cup was 45 mm. The bottom face of this container was in a state of being joined with a glass plate having a thickness of 2.2 mm on the outside of aluminum. Hereinafter, this container will be referred to as an aluminum glass cylindrical container.

[Freezing Step with Small Temperature Difference, and Drying Step]

An aqueous solution of CBE3 was poured respectively into the PTFE thick cylindrical container and the aluminum glass plate cylindrical container, and the aqueous solution of CBE3 was cooled through the bottom face using a cooling shelf board inside a vacuum freeze-drying machine (TF5-85ATNNN: Takara Co., Ltd.).

The container, the final concentration of the aqueous solution of CBE3, the liquid amount, and the setting of the shelf board temperature employed in this case were as described below.

Condition A:

PTFE thick cylindrical container, final concentration of the aqueous solution of CBE3: 4 mass %, amount of the aqueous solution: 4 mL. Regarding the setting of the shelf board temperature, cooling was performed until the temperature reached −10° C., and freezing was performed for 1 hour at −10° C., subsequently for 2 hours at −20° C., for 3 hours at −40° C., and lastly for 1 hour at −50° C. Subsequently, the shelf board temperature was returned to the setting of −20° C., and then the present frozen product was subjected to vacuum drying for 24 hours at −20° C. After 24 hours, while vacuum drying was still continued, the shelf board temperature was raised to 20° C., and vacuum drying was performed for another 48 hours at 20° C. until the degree of vacuum sufficiently decreased (1.9×10$^5$ Pa). Subsequently, the frozen product was removed from the vacuum freeze-drying machine. Thus, a porous body was obtained.

Condition B:

Aluminum glass plate cylindrical container, final concentration of aqueous solution of CBE3: 4 mass %, amount of the aqueous solution: 4 mL. Regarding the setting of the shelf board temperature, cooling was performed until the temperature reached −10° C., and freezing was performed for 1 hour at −10° C., subsequently for 2 hours at −20° C., for 3 hours at −40° C., and lastly for 1 hour at −50° C. Subsequently, the shelf board temperature was returned to the setting of −20° C., and then the present frozen product was subjected to vacuum drying for 24 hours at −20° C. After 24 hours, while vacuum drying was still continued, the shelf board temperature was raised to 20° C., and vacuum drying was performed for another 48 hours at 20° C. until the degree of vacuum sufficiently decreased (1.9×10$^5$ Pa). Subsequently, the frozen product was removed from the vacuum freeze-drying machine. Thus, a porous body was obtained.

Condition C:

PTFE thick cylindrical container, final concentration of the aqueous solution of CBE3: 4 mass %, amount of the aqueous solution: 10 mL. Regarding the setting of the shelf board temperature, cooling was performed until the temperature reached −10° C., and freezing was performed for 1 hour at −10° C., subsequently for 2 hours at −20° C., for 3 hours at −40° C., and lastly for 1 hour at −50° C. Subsequently, the shelf board temperature was returned to the setting of −20° C., and then the present frozen product was subjected to vacuum drying for 24 hours at −20° C. After 24 hours, while vacuum drying was still continued, the shelf board temperature was raised to 20° C., and vacuum drying was performed for another 48 hours at 20° C. until the degree of vacuum sufficiently decreased (1.9×10$^5$ Pa). Subsequently, the frozen product was removed from the vacuum freeze-drying machine. Thus, a porous body was obtained.

[3] Measurement of temperature difference in various freezing steps

In regard to each of Condition A to Condition C, the liquid temperature of the liquid surface at the circle center in the container was measured as the liquid temperature at the remotest place from the cooling side (non-cooling surface liquid temperature) within the solution, and the liquid temperature at the bottom in the container was measured as the liquid temperature closest to the cooling side (cooling surface liquid temperature) within the solution.

Figure 2:
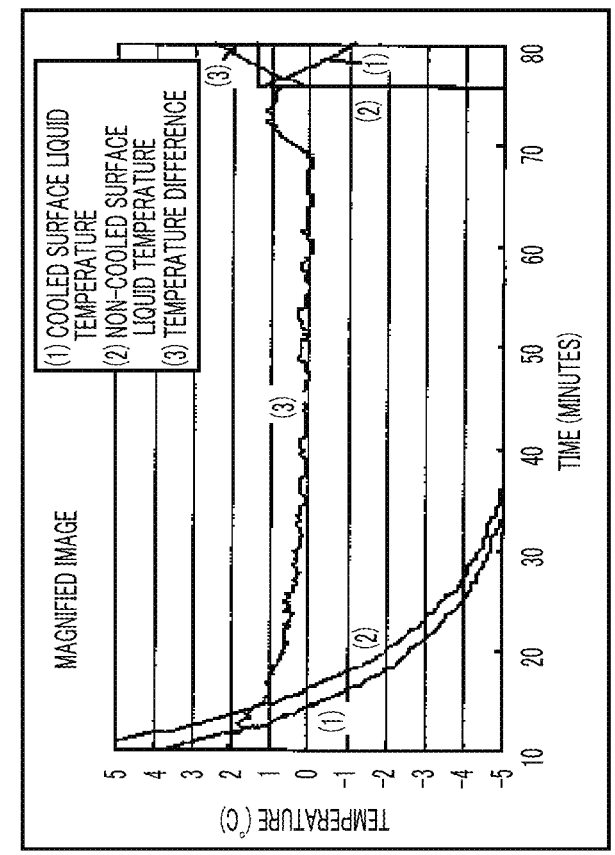
FIG. 2 illustrates a liquid temperature profile obtained under Condition B.
Figure 2:
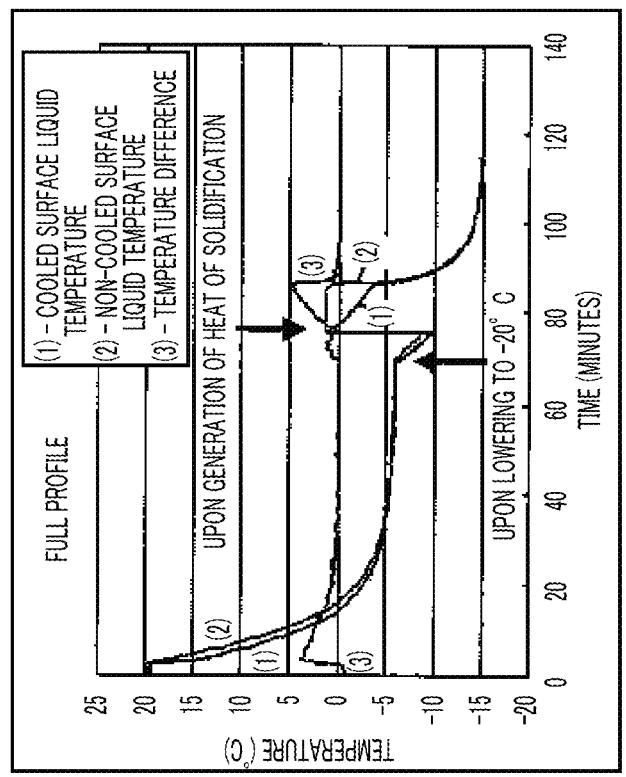
Figure 3:
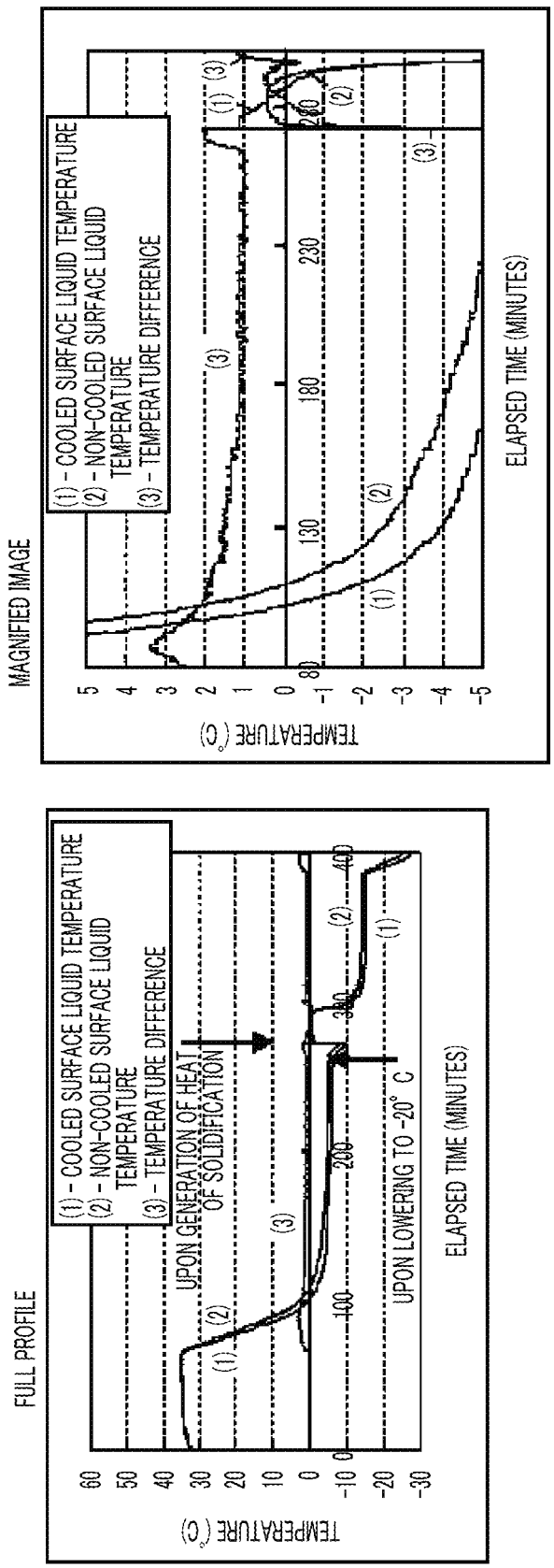
FIG. 3 illustrates a liquid temperature profile obtained under Condition C.

As a result, the profiles of the respective temperatures and the temperature differences were obtained as shown in FIG. 1 to FIG. 3.

From these FIG. 1, FIG. 2, and FIG. 3, it can be seen that under Condition A, Condition B, and Condition C, the liquid temperature was below the melting point, 0° C., in the section with the shelf board temperature set at −10° C. (before lowering to −20° C.), and that state was a state in which freezing had not occurred (unfrozen/overcooled). In this state, the temperature difference between the cooling surface liquid temperature and the non-cooling surface liquid temperature was 2.5° C. or less. Subsequently, as the shelf board temperature was further lowered to −20° C., a time point at which the liquid temperature rapidly increased to near 0° C. was confirmed. Thus, it is understood that the heat of solidification was generated here, and freezing was initiated. It could also be confirmed that ice formation had actually started at that time point. Subsequently, a certain time elapsed while the temperature remained at near 0° C. Here, a state in which water and ice existed as a mixture was maintained. Lastly, temperature drop started again from 0° C.; however, at this time, the liquid portion had disappeared, and only ice was left. Therefore, the temperature that was measured was the solid temperature inside the ice, and this was not a liquid temperature.

In the following description, the temperature difference at the time when the non-cooling surface liquid temperature reached the melting point (0° C.), the temperature difference immediately before lowering of the shelf board temperature from −10° C. to −20° C., and the temperature difference immediately before the generation of the heat of solidification will be described in conjunction with Condition A, Condition B, and Condition C. The "temperature difference immediately before" as used in the present specification means the largest temperature difference among the temperature differences detectable in a period between 1 second and 20 seconds before the main event.

Condition A

Temperature difference at the time when the liquid temperature of the non-cooling surface reached the melting point (0° C.): 1.1° C.

Temperature difference immediately before lowering from −10° C. to −20° C.: 0.2° C. Temperature difference immediately before the generation of the heat of solidification:

1.1° C.

Condition B

Temperature difference at the time when the liquid temperature of the non-cooling surface reached the melting point (0° C.): 1.0° C.

Temperature difference immediately before lowering from −10° C. to −20° C.: 0.1° C.

Temperature difference immediately before the generation of the heat of solidification: 0.9° C.

Condition C

Temperature difference at the time when the liquid temperature of the non-cooling surface reached the melting point (0° C.): 1.8° C.

Temperature difference immediately before lowering from −10° C. to −20° C.: 1.1° C.

Temperature difference immediately before the generation of the heat of solidification: 2.1° C.

Hereinafter, these will be referred to as "freezing step with small temperature difference/porous body".

[4] Freezing step with small temperature difference in 1 mass % ethanol-containing solution, and drying step A 1 mass % (w/w) ethanol-containing aqueous solution of CBE3 was respectively poured into the PTFE thick cylindrical container and the aluminum glass plate cylindrical container, and the aqueous solution of CBE3 was cooled through the bottom face using a cooling shelf board inside a vacuum freeze-drying machine (TF5-85ATNNN: Takara Co., Ltd.). Since an ethanol-containing aqueous solution at a final concentration of 1 mass % was used, the melting point was −0.4° C. The melting point change at the ethanol/water concentration ratio was calculated from literature "Pickering S. U.: A Study of the Properties of Some Strong Solutions. J. Chem. Soc. London, 63 (1893), 998-1027".

The container, the final concentration of the aqueous solution of CBE3, the liquid amount, and the setting of the shelf board temperature employed in this case were as described below.

Condition AA:

PTFE thick cylindrical container, final concentration of the aqueous solution of CBE3: 4 mass %, final ethanol concentration: 1 mass %, amount of the aqueous solution: 4 mL. Regarding the setting of the shelf board temperature, cooling was performed until the temperature reached −10° C., and freezing was performed for 1 hour at −10° C., subsequently for 2 hours at −20° C., for 3 hours at −40° C., and lastly for 1 hour at −50° C. Subsequently, the shelf board temperature was returned to the setting of −20° C., and then the present frozen product was subjected to vacuum drying for 24 hours at −20° C. After 24 hours, while vacuum drying was still continued, the shelf board temperature was raised to 20° C., and vacuum drying was performed for another 48 hours at 20° C. until the degree of vacuum sufficiently decreased. Subsequently, the frozen product was removed from the vacuum freeze-drying machine. Thus, a porous body was obtained.

Condition BB:

Aluminum glass plate cylindrical container, final concentration of the aqueous solution of CBE3: 4 mass %, final ethanol concentration: 1 mass %, amount of the aqueous solution: 4 mL. Regarding the setting of the shelf board temperature, cooling was performed until the temperature reached −10° C., and freezing was performed for 1 hour at −10° C., subsequently for 2 hours at −20° C., for 3 hours at −40° C., and lastly for 1 hour at −50° C. Subsequently, the shelf board temperature was returned to the setting of −20° C., and then the present frozen product was subjected to vacuum drying for 24 hours at −20° C. After 24 hours, while vacuum drying was still continued, the shelf board temperature was raised to 20° C., and vacuum drying was performed for another 48 hours at 20° C. until the degree of vacuum sufficiently decreased. Subsequently, the frozen product was removed from the vacuum freeze-drying machine. Thus, a porous body was obtained.

[Measurement of Temperature Difference of 1 Mass % Ethanol-Containing Solution in Freezing Step]

In regard to Condition AA and Condition BB, the liquid temperature of the liquid surface at the circle center in the container was measured as the liquid temperature at the remotest place from the cooling side (non-cooling surface liquid temperature) within the solution, and the liquid temperature at the bottom in the container was measured as the liquid temperature closest to the cooling side (cooling surface liquid temperature) within the solution. Here, since 1 mass % ethanol was used as the solvent, the solvent melting point was −0.4° C. The melting point change at the ethanol/water concentration ratio was calculated from literature "Pickering S.U.: A Study of the Properties of Some Strong Solutions. J. Chem. Soc. London, 63 (1893), 998-1027".

Figure 4:
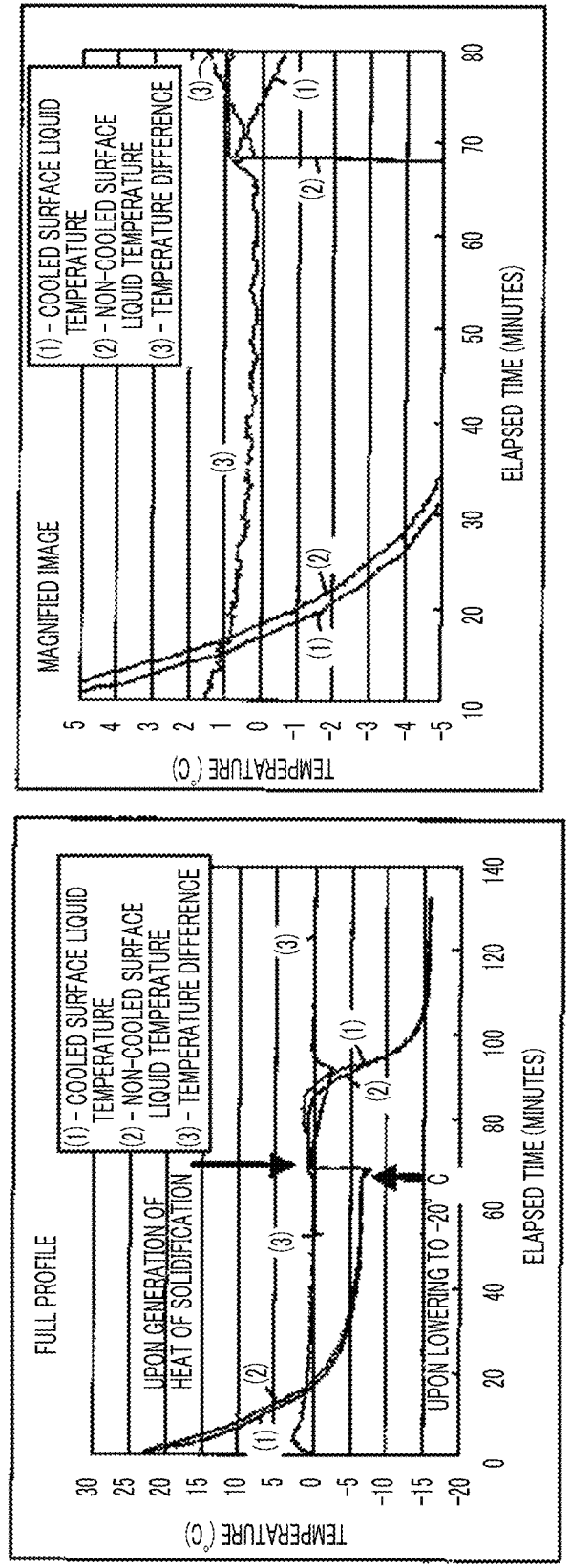
FIG. 4 illustrates a liquid temperature profile obtained under Condition AA.
Figure 5:
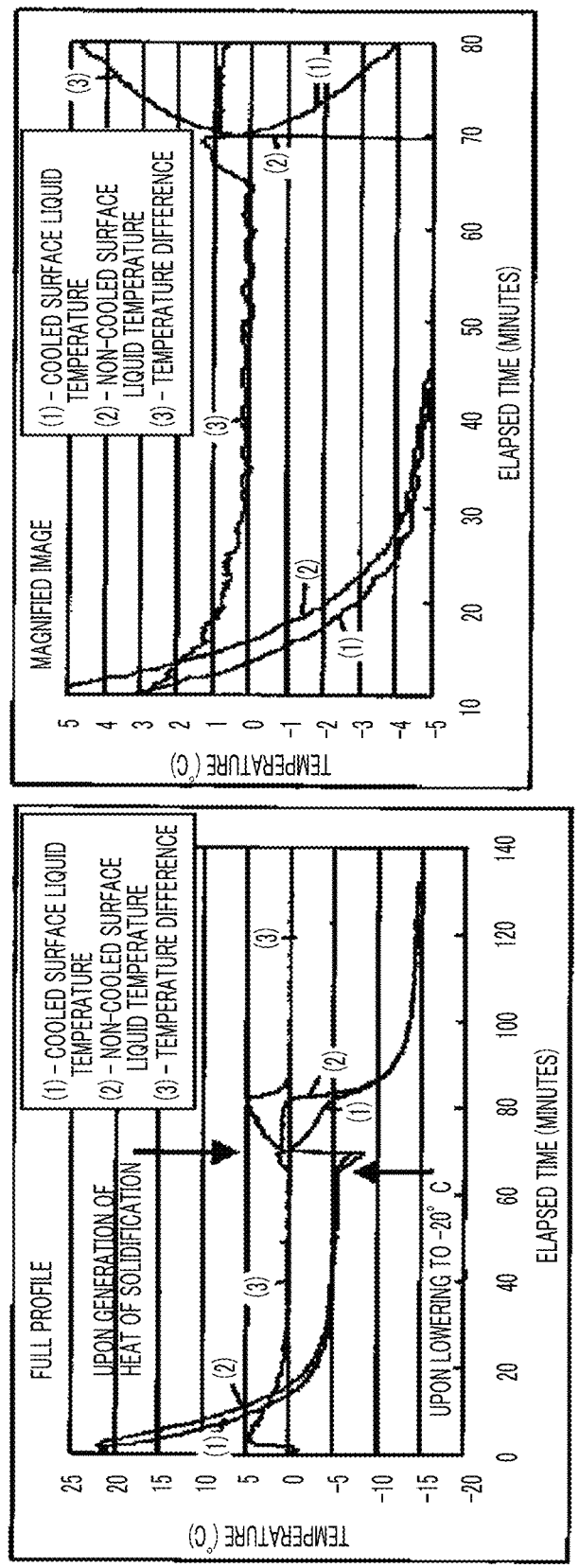
FIG. 5 illustrates a liquid temperature profile obtained under Condition BB.
Figure 6:
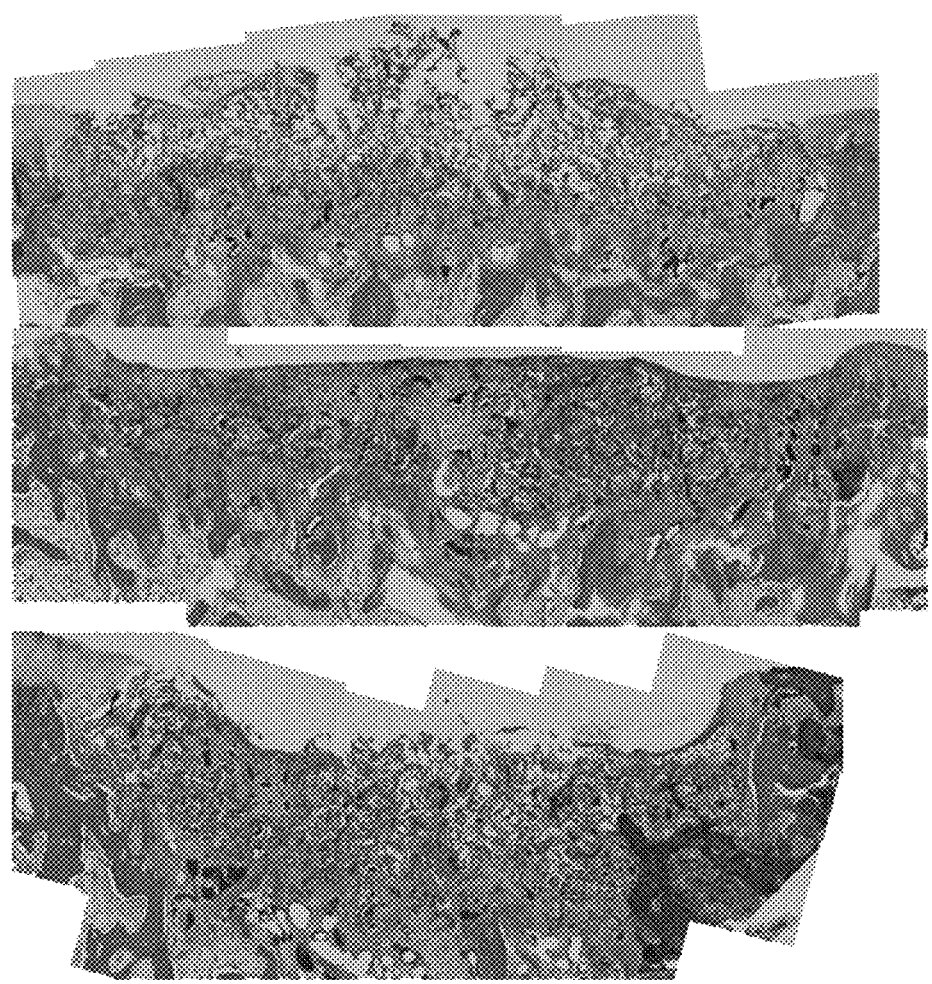
FIG. 6 shows the results of staining of a tissue onto which only a sponge was transplanted (without film).
Figure 7:
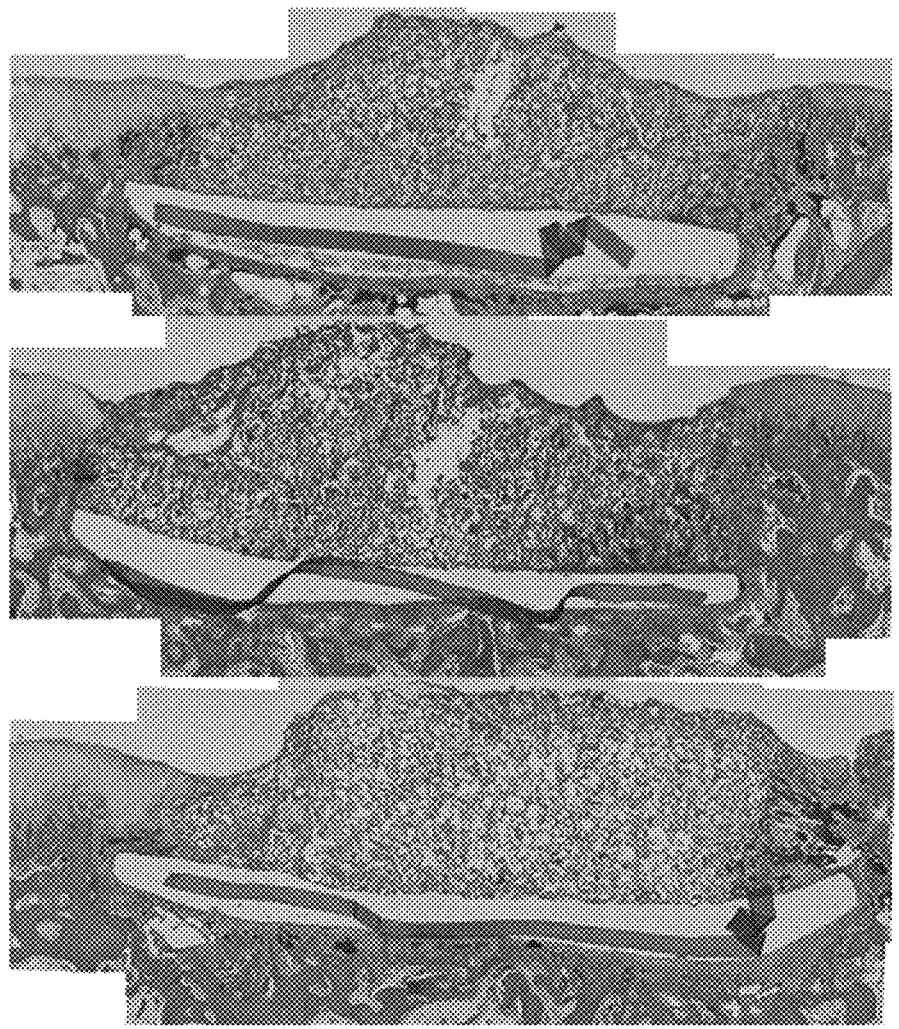
FIG. 7 shows the results of staining of a tissue onto which a sponge (without cells) and a film were transplanted.
Figure 8:
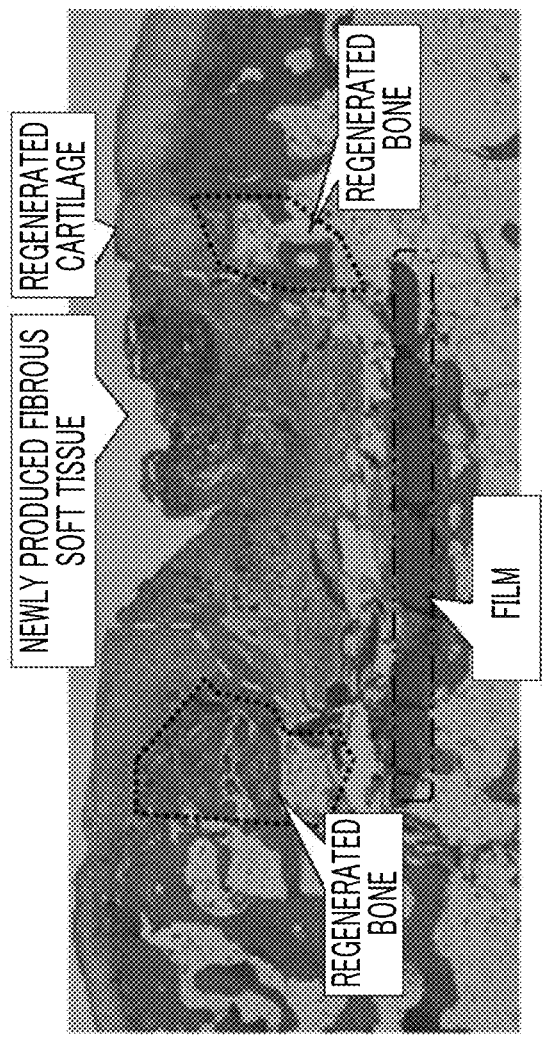
FIG. 8 shows the results of staining of a tissue onto which a cell culture sponge and a film have been transplanted.
Figure 8:
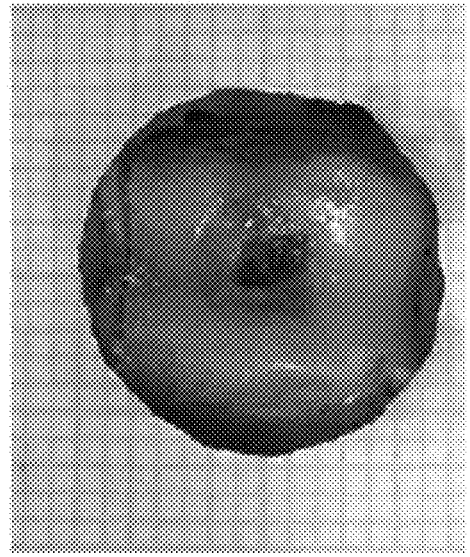
Figure 9:
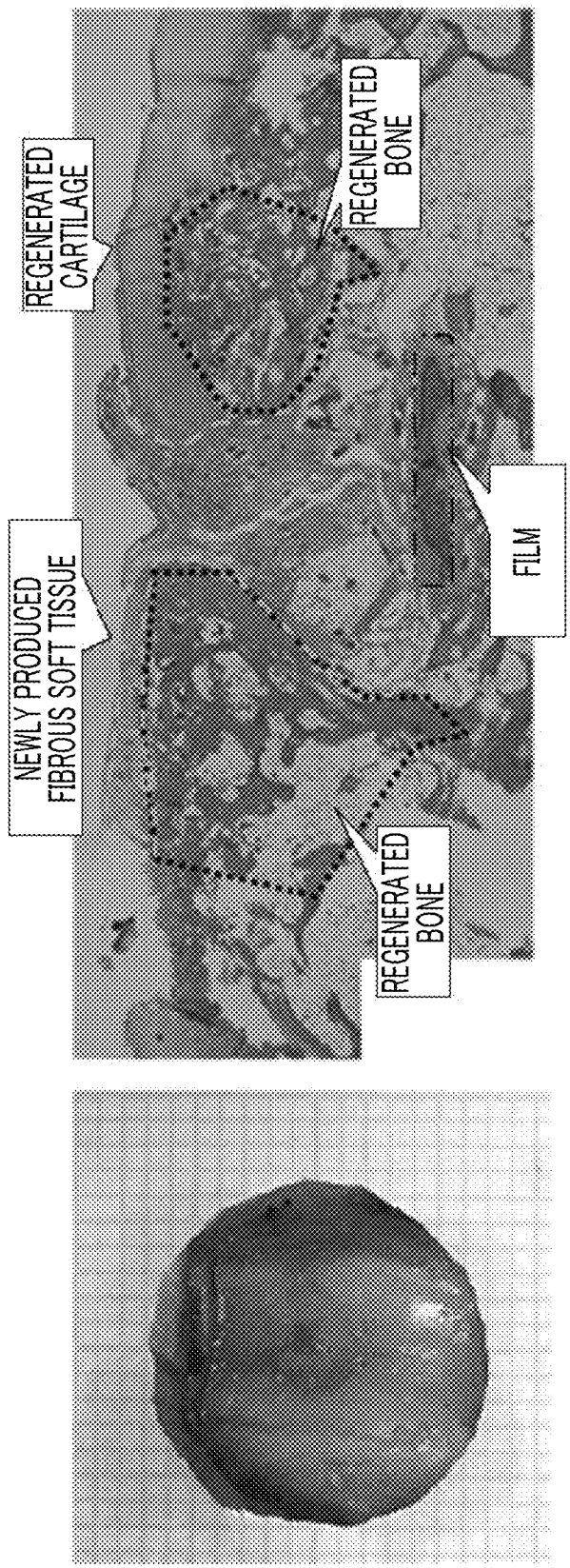
FIG. 9 shows the results of staining of a tissue onto which a cell mass and a film have been transplanted.
Figure 10:
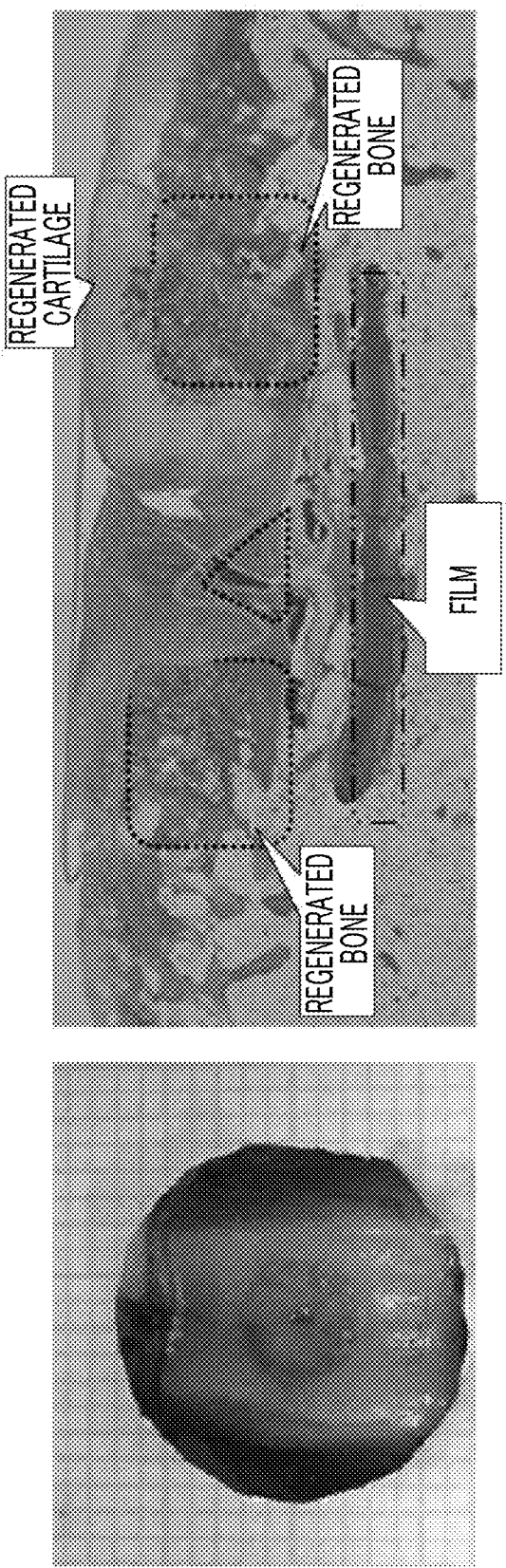
FIG. 10 shows the results of staining of a tissue onto which a mosaic cell mass and a film have been transplanted.

As a result, the profiles of the respective temperatures and the temperature differences were obtained as shown in FIG. 4 to FIG. 5. From these FIG. 4 and FIG. 5, it can be seen that under Condition AA and Condition BB, the liquid temperature was below the melting point, −0.4° C., in the section with the shelf board temperature set at −10° C., and that state was a state in which freezing had not occurred (unfrozen/overcooled). In this state, the temperature difference between the cooling surface liquid temperature and the non-cooling surface liquid temperature was 2° C. or less. Subsequently, as the shelf board temperature was further lowered to −20° C., a time point at which the liquid temperature rapidly increased to near −0.4° C. was confirmed. Thus, it is understood that the heat of solidification was generated here, and freezing was initiated. It could also be confirmed that ice formation had actually started at that time point. Subsequently, a certain time elapsed while the temperature remained at near −0.4° C. Here, a state in which water and ice existed as a mixture was maintained. Lastly, temperature drop started again from 0° C.; however, at this time, the liquid portion had disappeared, and only ice was left. Therefore, the temperature that was measured was the solid temperature inside the ice, and this was not a liquid temperature.

In the following description, the temperature difference at the time when the non-cooling surface liquid temperature reached the melting point (−0.4° C.), the temperature difference immediately before lowering of the shelf board temperature from −10° C. to −20° C., and the temperature difference immediately before the generation of the heat of solidification will be described in conjunction with Condition AA and Condition BB.

Condition AA

Temperature difference at the time when the liquid temperature of the non-cooling surface reached the melting point (−0.4° C.): 0.8° C.

Temperature difference immediately before lowering from −10° C. to −20° C.: 0.3° C.

Temperature difference immediately before the generation of the heat of solidification: 0.8° C.

Condition BB

Temperature difference at the time when the liquid temperature of the non-cooling surface reached the melting point (−0.4° C.): 1.3° C.

Temperature difference immediately before lowering from −10° C. to −20° C.: 0.0° C.

Temperature difference immediately before the generation of the heat of solidification: 1.3° C.

As a result, it was found that even under Condition AA and Condition BB, the porous body can be produced as "freezing step with small temperature difference/porous body", similarly to Condition A and Condition B.

[5] Production of petaloid blocks from freezing step with small temperature difference/porous body (pulverization and crosslinking of porous body)

Each of the CBE3 porous bodies of Condition A and Condition B obtained in the above section [2] (for the measurement of temperature difference, section [3]) was pulverized with a NEW POWER MILL (Osaka Chemical Co., Ltd., NEW POWER MILL PM-2005). Pulverization was carried out for 1 minute×5 times at the maximum rotation speed, for 5 minutes in total. The pulverization product thus obtained was classified by size with sieves made of stainless steel, and uncrosslinked blocks having sizes of 25 to 53 μm, 53 to 106 μm, and 106 μm to 180 μm were obtained. Subsequently, the uncrosslinked blocks were subjected to thermal crosslinking at 160° C. under reduced pressure (regarding the crosslinking time, six different times such as 8 hours, 16 hours, 24 hours, 48 hours, 72 hours, and 96 hours were employed), and thus sample CBE3 blocks were obtained. Hereinafter, the blocks originating from the porous body of Condition A, which were crosslinked for 48 hours, will be referred to as E, and the blocks originating from the porous body of Condition B, which were crosslinked for 48 hours, will be referred to as F. That is, E and F are small temperature difference blocks produced from freezing step with small temperature difference/porous bodies. Regarding the difference in the crosslinking time, since no influence on the performance was recognized in the evaluation of the present invention, products obtained by crosslinking for 48 hours were used herein as representative products. Furthermore, since consequently there was no difference observed between E and F in terms of performance, these were collectively used as petaloid blocks later.

[6] Method for Producing Recombinant Peptide Film

An aqueous solution of CBE3 at a concentration of 4 mass % was prepared, and 5.4 ml of this aqueous solution of CBE3 was caused to flow into a plastic tray provided with a silicon frame (8 cm×3.5 cm). This plastic tray was transferred into a refrigerator, and the aqueous solution was dried until no moisture left. Thus, a recombinant peptide film was obtained. The recombinant peptide film was taken out from the plastic tray/silicon frame, and was subjected to thermal crosslinking at 160° C. under reduced pressure (crosslinking time was 48 hours or 72 hours). Thus, samples for an animal test were obtained.

[7] Method for Measuring Degree of Crosslinking

The degree of crosslinking (number of crosslinks per molecule) of the film produced in the above section [6] was calculated. For the measurement, a TNBS (2,4,6-trinitrobenzenesulfonic acid) method was used.

<Preparation of Sample>

A sample (about 10 mg), a 4 mass % aqueous solution of $NaHCO_3$ (1 mL), and a 1 mass % aqueous solution of TNBS (2 mL) were introduced into a glass vial, and the mixture was shaken for 3 hours at 37° C. Subsequently, 37 mass % hydrochloric acid (10 mL) and pure water (5 mL) were added thereto, and then the mixture was left to stand for 16 hours or longer at 37° C. The resultant was used as a sample.

<Preparation of Blank>

A sample (about 10 mg), a 4 mass % aqueous solution of $NaHCO_3$ (1 mL), and a 1 mass % aqueous solution of TNBS (2 mL) were introduced into a glass vial, 37 mass % hydrochloric acid (3 mL) was added thereto immediately thereafter, and the mixture was shaken for 3 hours at 37° C. Subsequently, 37 mass % hydrochloric acid (7 mL) and pure water (5 mL) were added thereto, and then the mixture was left to stand for 16 hours or longer at 37° C. The resultant was used as a blank.

The light absorbance (345 nm) of a dilution of the sample obtained by diluting 10 times with pure water, and the light absorbance of the blank were measured, and the degree of crosslinking (number of crosslinks per molecule) was calculated from (Formula 2) and (Formula 3).

$$(As-Ab)/14600 \times V/w \qquad \text{(Formula 2)}$$

(Formula 2) represents the amount of lysine (molar equivalent) per gram of the recombinant peptide.

In Formula 2, As represents the light absorbance of the sample; Ab represents the light absorbance of the blank; V represents the amount of the reaction liquid (g); and w represents the mass (mg) of the recombinant peptide.

$$1-(\text{Sample (Formula 1)/uncrosslinked recombinant peptide (Formula 1)}) \times 34 \qquad \text{(Formula 3)}$$

(Formula 3) represents the number of crosslinks per molecule.

As a result, the film obtained by crosslinking for 48 hours in the above section [6] had a degree of crosslinking of 6, and the film obtained by crosslinking for 72 hours in the above section [6] had a degree of crosslinking of 13.

[8] Method for Measuring Rate of Decomposition

The rate of decomposition of the film produced in the above section [6] was evaluated.

5 mg of a sample produced in the above section [6] was introduced into a plastic tube, the mass of which had been measured in advance, and the actual amount of addition was recorded.

2.5 mg of Actinomyces-derived collagenase was dissolved in 50 ml of phosphate buffered saline (PBS), and a collagenase solution was obtained. 1 ml of this collagenase solution was added to the tube containing the sample, and the content was mixed by vortexing. Subsequently, the mixture was shaken for 5 hours at 37° C. Subsequently, the tube was centrifuged for 1 minute at 10,000G, and the supernatant was removed using a pipette. 1 ml of ultrapure water was added to the tube, and the content was mixed by vortexing. Subsequently, the tube was centrifuged for 1 minute at 10,000G, and the supernatant was removed using a pipette. This operation was repeated one more time. Subsequently, the sample was freeze-dried, and the mass of the tube containing the sample was recorded.

The rate of decomposition of the film was calculated from the following formula (Formula 4).

Rate of decomposition=$((W-We)-wo)/wo/T$     (Formula 4)

In Formula 4, W represents the mass of the tube containing the sample, which was recorded after freeze-drying; and We represents the blank mass of the tube that was recorded in advance. wo represents the actual amount of addition of the sample. T represents the time taken for shaking in the collagenase solution, and in this test, T was 5 hours.

As a result, the film of the above section [6] resulted in a rate of decomposition of 6.9 [mass %/hour] under cross-linking for 48 hours, and a rate of decomposition of 0.5 [mass %/hour] under crosslinking for 72 hours.

[9] Collection of Rabbit Mesenchymal Stem Cells (MSC)

The bone marrow aspirates of five Japanese white rabbits (3-week old male) were collected from 10 femurs and 10 tibias. First, the bones were disinfected with an isodine dilution and were washed with DULBECCO's phosphate buffered saline (DPBS). The bones were transferred onto a 10-cm dish, and both ends of each bone were cut with bone clippers. 5 mL of a medium dispensed in a 10-mL syringe equipped with an 18G needle was collected, a femur was taken using a Dispin, and the needle was pierced into the bone marrow on a 50-mL tube.

Subsequently, a medium was caused to flow into the bone marrow, and the bone marrow was collected into the 50-mL tube. The bone marrow aspirate thus collected was carefully pipetted and passed through a cell strainer. Subsequently, the bone marrow aspirate was centrifuged for 5 minutes at 1,000 rpm, subsequently the supernatant was removed, and the residue was suspended in a medium. Then, the suspension was inoculated into a flask. The medium was exchanged the next day after the inoculation, and adhered cells were collected 5 days after the inoculation. Thereby, collection of rabbit MSC cells was completed. Thereafter, the cells were subcultured for proliferation as appropriate for use. Regarding the medium used in the above procedure, a medium of DULBECCO's modified Eagle medium/high glucose (DMEM high glucose), 10 vol % fetal bovine serum (FBS), and penicillin/streptomycin (50,000 U) was used in all cases.

[10] Production of Mosaic Cell Mass using Petaloid Blocks (Rabbit MSC)

The rabbit bone marrow-derived mesenchymal stem cells (rabbit MSC) collected in the above section [9] were prepared into a suspension at a concentration of $1 \times 10^5$ cells/mL or $4 \times 10^5$ cells/mL using a medium, and the petaloid blocks 53-106 µm produced in the above section [5] were added thereto at a concentration of 0.1 mg/mL. Subsequently, 200 µL of the cell suspension thus obtained was inoculated onto a SUMILON CELL-TIGHT X96U plate (Sumitomo Bakelite, with a U-shaped bottom), and the cell suspension was centrifuged (600g, 5 minutes) using a tabletop plate centrifuge and left to stand for 24 hours. Thus, a spherical mosaic cell mass having a diameter of about 1 mm or a diameter of about 1.3 mm and formed from petaloid blocks and rabbit MSC cells was produced (0.001 µg of blocks per cell). Since the cell mass was produced in a U-shaped plate, this mosaic cell mass was spherical in shape. The mosaic cell mass produced at a density of $1 \times 10^5$ cells/mL is referred to as small mosaic cell mass, and the mosaic cell mass produced at a density of $4 \times 10^5$ cells/mL is referred to as large mosaic cell mass.

[11] Production of Cell Mass (Rabbit MSC)

The rabbit bone marrow-derived mesenchymal stem cells (rabbit MSC) collected in the above section [9] were prepared into a suspension at a concentration of $1 \times 10^5$ cells/mL or $4 \times 10^5$ cells/mL using a medium. 200 µL of the cell suspension thus obtained was inoculated onto a SUMILON CELL-TIGHT X96U plate (Sumitomo Bakelite, with a U-shaped bottom), and the cell suspension was centrifuged (600 g, 5 minutes) using a tabletop plate centrifuge and left to stand for 24 hours. Thereby, a spherical cell mass having a diameter of about 400 µm or a diameter of about 1 mm was produced. The cell mass produced at a density of $1 \times 10^5$ cells/mL is referred to as small cell mass, and the cell mass produced at a density of $4 \times 10^5$ cells/mL is referred to as large cell mass.

[12] Production of Cell Culture Sponge (Rabbit MSC)

A specimen having a diameter of 5 mm and a thickness of 1 mm was cut out from the CBE3 sponge produced under Condition AA in the above section [4], and the rabbit bone marrow-derived mesenchymal stem cells (rabbit MSC) collected in the above section [9] were inoculated into the sponge. Thus, a cell culture sponge was prepared.

[13] Production of Rabbit Osteochondral Defect Model

In a 22-week old male Japanese white rabbit (Kitayama Labes Co., Ltd., SPF), an osteochondral defect having a size with a diameter of 5 mm and a depth of about 1 mm was produced at a knee joint site.

[14] Sample transplantation into rabbit osteochondral defect

First, the film (having a degree of crosslinking of 6) prepared in the above section [6] and cut out into the bottom area size (diameter 5 mm) of the defect, was placed at the rabbit osteochondral defect site produced in the above section [13]. The following was transplanted thereon.

Comparative Example 2: Sponge without Cells, Obtained by Excluding the Process of Inoculating Cells in the Above Section [12]

Comparative Example 3: Cell Culture Sponge Produced in the Above Section [12]

Comparative Example 4: 144 Units of Small Cell Mass Produced in the Above Section [11]

Example 1: 144 Units of Small Mosaic Cell Mass Produced in the Above Section [10]

Furthermore, as another Comparative Example, a group in which only a sponge without cells was transplanted, without placing the film prepared in the above section [6] (Comparative Example 1), was also prepared.

[15] Bone/cartilage regeneration effect in rabbit osteochondral defect model

The rabbit that received transplantation in the above section [14] was autopsied after 8 weeks, and osteochondral tissue slices in the periphery of the transplantation site were produced. The tissue was fixated with formalin and embedded in paraffin. Thus, skin tissue slices including mosaic cell masses were produced. Staining of the slices was carried out by HE staining (hematoxylin-eosin staining) or safranin O staining.

The results of staining are shown in FIG. 6 to FIG. 10. Cartilage regeneration, bone regeneration, suppression of fibrous soft tissue, and formation of bone-cartilage interface were evaluated according to the following criteria. The evaluation criteria are presented in Table 1.

Cartilage regeneration
AA: Satisfactory cartilage regeneration is recognized in general.
A: Cartilage regeneration is recognized in general.
B: Slight cartilage regeneration is recognized in some part.
C: Cartilage regeneration is not recognized.

Bone Regeneration
A: Bone regeneration is recognized.
B: Slight bone regeneration is recognized in some parts.
C: Bone regeneration is not recognized.

Suppression of Infiltration of Fibrous Soft Tissue
A: Suppression of the infiltration of fibrous soft tissue is recognized.
B: Suppression of the infiltration of fibrous soft tissue is slightly recognized.
C: Suppression of the infiltration of fibrous soft tissue is not recognized.
D: Infiltration of inflammation cannot be suppressed, and suppression of the infiltration of fibrous soft tissue is poorly achieved.

Formation of Bone-Cartilage Interface
A: A boundary line (tidemark) between regenerated bone and regenerated cartilage is formed at a right position.
B: A boundary line (tidemark) between regenerated bone and regenerated cartilage is formed to a slight extent.
C: A boundary line (tidemark) between regenerated bone and regenerated cartilage is not formed.

TABLE 1

|  |  | Cartilage regeneration | Bone regeneration | Suppression of fibrous soft tissue | Formation of bone/cartilage interface |
| --- | --- | --- | --- | --- | --- |
| Comparative Example 1 | Sponge only transplanted (without film) (FIG. 6) | C | C | D | C |
| Comparative Example 2 | Sponge (without cells) and film transplanted (FIG. 7) | C | C | B | C |
| Comparative Example 3 | Cell culture sponge and film transplanted (FIG. 8) | B | B | D | C |
| Comparative Example 4 | Cell mass and film transplanted (FIG. 9) | B | A | C | C |
| Example 1 (Present invention) | Mosaic cell mass and film transplanted (FIG. 10) | AA | A | A | A |

In the case in which only a sponge was transplanted (without film) (FIG. 6) and in the case in which a sponge (without cells) and a film were transplanted (FIG. 7), cartilage regeneration was not recognized, and bone regeneration was also not recognized.

In the case in which a cell culture sponge and a film were transplanted (FIG. 8), slight cartilage regeneration and bone regeneration were recognized in some parts; however, most of the tissue became a fibrous soft tissue, and cartilage regeneration and bone regeneration were not successful.

In the case in which a cell mass and a film were transplanted (FIG. 9), slight cartilage regeneration was recognized in some parts, and bone regeneration was also recognized; however, a fibrous tissue was generated in most of the positions where cartilage should have been generated. Thus, cartilage regeneration and bone regeneration were not successful.

In the case in which a mosaic cell mass and a film were transplanted (FIG. 10), satisfactory cartilage regeneration was recognized in general, and a boundary line (tidemark) between regenerated bone and regenerated cartilage was formed at a right position. Bone regeneration was also recognized at a right position, hardly any fibrous soft tissue was formed, and satisfactory cartilage regeneration and bone regeneration could be achieved.

[Sequence List]

International Application Application 15F02882 Cartilage Regenerative Material JP 16058540 20160317-00110214551600554135 Normal 20160317153508201602221618251590_P1AP101_15_1.app Based on International Reception Patent Cooperation Treaty

What is claimed is:

1. A method for regenerating cartilage and bone, the method comprising transplanting a cell construct that includes biocompatible polymer blocks and stem cells to a patient in need of cartilage generation, in which the cell construct has a plurality of the biocompatible polymer blocks disposed in gaps between a plurality of the stem cells, wherein the cell construct and a biocompatible polymer film is transplanted, wherein the biocompatible polymer film is present between the transplantation site and the cell construct, and
wherein the bone and cartilage are generated at the same time.

2. The method of according to claim 1, wherein the cell construct is transplanted to a diseased site of cartilage defect.

3. The method of according to claim 1, wherein the stem cells are mesenchymal stem cells (MSC), amniotic cells, cord blood-derived cells, bone marrow-derived cells, or adipose-derived stem cells.

4. The method according to claim 1, wherein the stem cells are mesenchymal stem cells (MSC).

5. The method according to claim 1, wherein the biocompatible polymer film is a biodegradable polymer.

6. The method according to claim 1, wherein the cell construct includes the biocompatible polymer blocks in an amount of from 0.0000001 μm to 1 μg per stem cell.

7. The method according to claim 1, wherein the size of each of the biocompatible polymer blocks is from 10 μm to 300 μm.

8. The method according to claim 1, wherein the cell construct has a thickness or diameter of from 100 μm to 1 cm.

9. The method according to claim 1, wherein the biocompatible polymer blocks comprise a recombinant peptide or a chemically synthesized peptide.

10. The method according to claim 1, wherein the biocompatible polymer blocks comprise a recombinant gelatin or a chemically synthesized gelatin.

11. The method according to claim 1, wherein the biocompatible polymer blocks comprise a recombinant gelatin or a chemically synthesized gelatin represented by Formula 1,

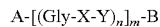  Formula 1:

in Formula 1, n units of X each independently represent any amino acid residue; n units of Y each independently represent any amino acid residue; m represents an integer from 2 to 10;
n represents an integer from 3 to 100; A represents an arbitrary amino acid residue or amino acid sequence; and B represents an arbitrary amino acid residue or amino acid sequence.

12. The method according to claim 1, wherein the biocompatible polymer blocks comprise any of the following:
a peptide comprising the amino acid sequence set forth in SEQ ID NO:1;
a peptide having biocompatibility and comprising an amino acid sequence obtained by modifying the amino acid sequence set forth in SEQ ID NO:1 by deletion, substitution or addition of one or several amino acid residues; or
a peptide having biocompatibility and comprising an amino acid sequence having at least 80% sequence identity with the amino acid sequence set forth in SEQ ID NO:1.

13. The method according to claim 1, wherein biocompatible polymers in the biocompatible polymer blocks are crosslinked by heat, ultraviolet radiation, or an enzyme.

14. The method according to claim 1, wherein the biocompatible polymer blocks are in the form of granules obtainable by pulverizing a porous body of a biocompatible polymer.

15. The method according to claim 1 wherein the cell construct and a biocompatible polymer film is transplanted, and the biocompatible polymer film is a film for isolating a portion or the entirety of the transplant face of the cell construct from the site of transplantation.

* * * * *